US009060693B2

(12) United States Patent
Kawamura

(10) Patent No.: US 9,060,693 B2
(45) Date of Patent: Jun. 23, 2015

(54) VISUAL FUNCTION TESTING DEVICE

(71) Applicant: PANASONIC CORPORATION, Osaka (JP)

(72) Inventor: Ryo Kawamura, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 14/148,657

(22) Filed: Jan. 6, 2014

(65) Prior Publication Data
US 2014/0118685 A1 May 1, 2014

Related U.S. Application Data

(63) Continuation of application No. 13/656,476, filed on Oct. 19, 2012, now Pat. No. 8,657,444, which is a continuation of application No. PCT/JP2011/059370, filed on Apr. 15, 2011.

(30) Foreign Application Priority Data

Apr. 21, 2010 (JP) ................................ 2010-097833

(51) Int. Cl.
A61B 3/02 (2006.01)
A61B 3/032 (2006.01)
(Continued)

(52) U.S. Cl.
CPC . *A61B 3/02* (2013.01); *A61B 3/032* (2013.01); *A61B 3/08* (2013.01); *A61B 3/024* (2013.01)

(58) Field of Classification Search
CPC ...... A61B 3/0083; A61B 3/024; A61B 3/028; A61B 3/032; A61B 3/18
USPC ......... 351/201, 205, 210, 211, 221, 222, 224, 351/237, 239, 240, 243, 246
See application file for complete search history.

(56) References Cited

U.S. PATENT DOCUMENTS 7,784,948 B2 * 8/2010 Nozawa et al. ................ 351/211
8,657,444 B2 * 2/2014 Kawamura .................... 351/240
(Continued)

FOREIGN PATENT DOCUMENTS

JP 3168056 B2 5/2001
JP 2003-093344 A 4/2003
(Continued)

OTHER PUBLICATIONS

Hiroko Nakayama et al., "A proposal of the multipurpose ophthalmic test equipment by applying virtual reality technology", The Virtual Reality Society of Japan, the 13th Annual Conference Ronbunshu, Sep. 2008, pp. 329-332.
(Continued)

*Primary Examiner* — Huy K Mai
(74) *Attorney, Agent, or Firm* — McDermott Will & Emery LLP

(57) ABSTRACT

A visual function testing device includes: a visual target image presentation unit that presents a visual target image; a visual target image rendering unit that renders the visual target image to be presented on the visual target image presentation unit; a visual function test item selection unit that selects a visual function test item; a visual target image generation unit that generates a visual target image corresponding to the test item selected by the visual function test item selection unit; a viewpoint distance input unit that inputs a distance between the visual target image presentation unit and a viewpoint of an observer; and a visual angle input unit that inputs an angle to be made by the visual target image and the viewpoint of the observer. Based on the viewpoint distance and the visual angle, a display size and display position of a visual target image are calculated.

3 Claims, 14 Drawing Sheets

(51) Int. Cl.
  *A61B 3/08* (2006.01)
  *A61B 3/024* (2006.01)

(56) References Cited

U.S. PATENT DOCUMENTS

2008/0259278 A1   10/2008   Nozawa et al.
2010/0201948 A1*   8/2010   Sahraie et al. ............... 351/239

FOREIGN PATENT DOCUMENTS

| JP | 2008-229175 A | 10/2008 |
| JP | 2008-264267 A | 11/2008 |
| JP | 2009-131326 A | 6/2009 |
| JP | 2009-153574 A | 7/2009 |
| JP | 2009-178500 A | 8/2009 |
| JP | 2010-075755 A | 4/2010 |
| WO | 2009/075385 A1 | 6/2009 |

OTHER PUBLICATIONS

International Search Report mailed Jun. 14, 2011 issued in corresponding International Application No. PCT/JP2011/059370.
Non-Final Office Action issued in U.S. Appl. No. 13/656,476 dated May 31, 2013.
Corrected Notice of Allowance issued in U.S. Appl. No. 13/656,476 dated Oct. 7, 2013.

* cited by examiner (a) FLAT TYPE (b) ARCH TYPE (c) DOME TYPE (d) MULTI-SURFACE TYPE
(EXAMPLE: THREE-SURFACE)

(a)

(b)

(c)

(a)

(b)

VISUAL FUNCTION TESTING DEVICE

This application is a Continuation of U.S. patent application Ser. No. 13/656,476, filed Oct. 19, 2012, now U.S. Pat. No. 8,657,444, which is based on International Application No. PCT/JP2011/059370, filed Apr. 15, 2011, claiming the foreign priority of Japanese Patent Application No. 2010-097833, filed Apr. 21, 2010, the contents each of which are incorporated herein by reference.

TECHNICAL FIELD

The present disclosure relates to a visual function testing device that performs a plurality of visual function tests by itself.

BACKGROUND

Heretofore, visual function testing devices for testing a variety of visual functions have been known. In visual function tests in the ophthalmic treatment, there are many test items. As the test items concerned, there are visual acuity and field tests, a binocular vision test, an eye position test, and the like. The visual function testing devices for the variety of visual function tests as described above are configured according to specifications specialized for test contents of the respective items such as the visual acuity and the visual field, and accordingly, there is not a visual function testing device capable of testing the visual acuity, the visual field and the binocular vision by itself.

As the visual function testing devices, there are known visual function testing devices, each of which is capable of performing two items of the visual function tests as described in Patent Literature 1 and Patent Literature 2, which are described below.

The visual function testing device described in Patent Literature 1 (Japanese Patent No. 3168056) has a function to present visual targets individually to left and right eyes by a dichoptic method using an optical system, a polarization filter, and a red/green filter, and in the same tester, uses such a visual target for the visual acuity test and such a visual target for the binocular vision test. In such a way, the visual function testing device of Patent Literature 1 can perform two visual function tests, which are the visual acuity test and the binocular vision test, by itself.

The visual function testing device described in Patent Literature 2 (Japanese Patent Laid-Open Publication No. 2003-93344) is a device configured in such a manner that a liquid crystal display for the visual acuity test is arranged on a center thereof, and that a light source for the visual field test, which is composed of a large number of LEDs, is arranged on a periphery of the liquid crystal display. In such a way, the visual function testing device of Patent Literature 2 can perform two visual function tests, which are the visual acuity test and the visual field test.

SUMMARY

Technical Problem

However, with regard to the visual function testers using the above-mentioned technology, there are instruments individually dedicated for the test items, and there is not a visual function testing device capable of testing more than two visual functions such as the visual acuity, the visual field, stereopsis, the binocular vision and the eye position.

Moreover, in the current visual acuity tester and visual field tester, a visual field of one eye is blocked by using an occluder and the like, and the tests are performed for each eye.

Moreover, since the current binocular vision tester realizes dichoptic viewing by means of a structure of looking into a lens barrel, the visual field is restricted, and accordingly, is narrowed. As described above, the current visual function testers block the visual field by the occluder and restrict the visual field by the lens barrel, and thereby implement the visual function tests in a state where visual performance is different from a daily one.

It is one of the objectives of the present disclosure to provide a visual function testing device for performing the plurality of visual function tests by itself in a state where both eyes are opened and a state where visual performance is close to the daily one without restricting the visual field.

Solution to Problem

A visual function testing device according to a first example of the present disclosure is a visual function testing device for testing a plurality of visual functions. The visual function testing device includes a visual target image presenting unit for presenting a visual target image; a visual target image rendering unit for rendering the visual target image to be presented on the visual target image presenting unit; a visual function test item selecting unit for selecting an item of a visual function test; a visual target image generating unit for generating a visual target image corresponding to the item of the test, the item being selected by the visual function test item selecting unit; a viewpoint distance inputting unit for inputting a distance between the visual target image presenting unit and a viewpoint of an observer; and a visual angle inputting unit for inputting an angle to be made by the visual target image and the viewpoint of the observer. Based on a viewpoint distance inputted by the viewpoint distance inputting unit and on the visual angle inputted by the visual angle inputting unit, the visual target image rendering unit calculates a display size and display position of a visual target image corresponding to a visual acuity or visual field test selected by the visual function test item selecting unit, and renders the visual target image with the calculated display size at the calculated display position.

In a second example of the present disclosure as the visual function testing device according to the first example, the visual target image generating unit has a binocular visual target image generation function to generate visual target images for each of a right eye and left eye of a subject, the visual target image presenting unit presents dichoptic visual target images for the right and the left eye, respectively, the dichoptic visual target images being separated for the right eye and the left eye from the binocular visual target images generated by the visual target image generating unit, the visual function testing device further includes a visual target image selection presenting unit configured to select display or non-display of a right visual target image for the right eye or a left visual target image for the left eye independently with each other, the right and left visual target images being to be presented by the visual target image presenting unit, and the visual target image selection presenting unit displays a visual target image corresponding to the stereopsis test selected by the visual function test item selecting unit.

A third example of the present disclosure as the visual function testing device according to the second example further includes a visual target image operating unit for changing at least one of the display size or display position of the visual target image by an operation of a user. In a case where a binocular vision test or an eye position test is selected by the visual function test item selecting unit, the visual target image rendering unit changes the visual target image to the display size and the display position, which are calculated by the visual target image rendering unit, in accordance with the display size or the display position of the visual target image changed by the visual target image operating unit.

In a fourth example of the present disclosure as the visual function testing device according to any one of the first to third examples, the visual target image rendering unit has a visual target image adjusting unit for adjusting brightness, contrast, color and transparency of the visual target image.

A fifth example of the present disclosure as the visual function testing device according to any one of the first to fourth examples further includes: a viewing angle inputting unit for inputting a viewing angle for use in the visual field test in a case where the visual field test is selected by the visual function test item selecting unit; and a viewpoint distance calculating unit for calculating a viewpoint distance to be required for implementing the visual field test at the viewing angle inputted by the viewing angle inputting unit in a screen dimension of the visual target image presenting unit.

A sixth example of the present disclosure as the visual function testing device according to any one of the first to fifth examples further includes: a visual acuity inputting unit for inputting visual acuity for use in the visual acuity test in a case where the visual acuity test is selected by the visual function test item selecting unit; and a viewpoint distance calculating unit for calculating a viewpoint distance to be required for implementing the visual acuity test at the visual acuity inputted by the visual acuity inputting unit in a resolution of the visual target image presenting unit.

A seventh example of the present disclosure as the visual function testing device according to any one of the second to sixth examples further includes: a parallax inputting unit for inputting a parallax for use in the stereopsis test in a case where the stereopsis test is selected by the visual function test item selecting unit; and a viewpoint distance calculating unit for calculating a viewpoint distance to be required for implementing the stereopsis test at the parallax inputted by the parallax inputting unit in the resolution of the visual target image presenting unit.

An eighth example of the present disclosure as the visual function testing device according to any one of the first to seventh examples further includes: a viewpoint distance measuring unit for measuring a distance between the visual target image presenting unit and the viewpoint of the observer. The measured viewpoint distance is inputted to the viewpoint distance inputting unit.

A ninth example of the present disclosure as the visual function testing device according to any one of the second to eighth examples further includes: a visual target image storing unit for storing the visual target image generated by the visual target image generating unit; a display setting storing unit for storing the display size and the display position of the visual target image, which are calculated by using the viewpoint position inputted by the viewpoint distance inputting unit and using visual angle inputted by the visual angle inputting unit; a visual target image selection storing unit for storing the display or non-display of the visual target image for each of the right eye and the left eye, the display or the non-display being set by the visual target image selection presenting unit; and a display order setting unit for setting a display order of a plurality of the visual target images by using in combination plural pieces of information stored in the respective storing unit, the visual target images being stored in the visual target image storing unit. In accordance with the display order set by the display order setting unit, the visual target images stored in the visual target image storing unit are called out, and are rendered by the visual target image rendering unit.

A tenth example of the present disclosure as the visual function testing device according to any one of the first to ninth examples further includes: an output unit for outputting test results of the visual function tests selected by the visual function test item selecting unit. The test results corresponding to the respective test items are outputted in a predetermined format.

Advantageous Effects

In accordance with the present technologies disclosed herein, the display size and the display position of the visual target image are calculated based on the inputted viewpoint distance and visual angle, and the visual target image is rendered. Accordingly, without blocking the visual field or restricting the viewing field, the plurality of visual function tests can be performed by the same device in a state where both eyes are opened and a state where the visual performance is close to the daily one in which the viewing field is not restricted.

BRIEF DESCRIPTION OF DRAWINGS

FIG. 3(a) is a flat type; FIG. 3(b) is an arch type; FIG. 3(c) is a dome type; and FIG. 3(d) is a multi-surface type.

FIGS. 4(a), 4(b) and 4(c) are explanatory views of sizes of a Landolt ring, a radiant, and a visual target image, respectively.

FIG. 8(a) is a case where the screen center is set at a position directly confronted to the viewpoint position; and FIG. 8(b) is a case where the screen center is set at a position directly confronted to a left eye.

DESCRIPTION OF EMBODIMENTS

Figure 1:
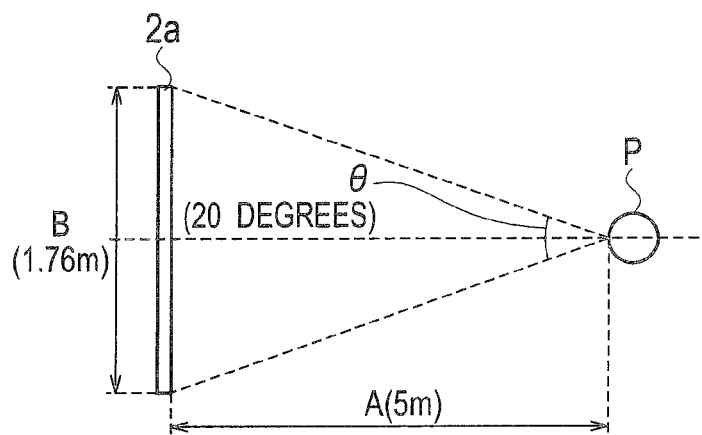
FIG. 1 is a side view showing a relationship between a viewpoint position P and a presentation surface of a visual target image presentation unit in a visual function testing device to be shown as an embodiment of the present disclosure.

A description is made below of embodiments of the present disclosure with reference to the drawings.

First Embodiment

A visual function testing device of a first embodiment of the present disclosure is a device that can implement a plurality of visual function tests in a state where both eyes are opened, which is a state where visual performance is close to daily visual performance, and can evaluate the daily visual performance in many sides. This visual function testing device can perform the plurality of visual function tests by itself. Such visual function tests are tests for functions which work for viewing, and are broadly classified into subjective tests and multisensitive tests. The subjective tests are tests such as visual acuity, visual field and binocular vision tests, which are frequently performed in ophthalmic treatment. As opposed to this, the objective tests are performed in such a case where a response of a patient cannot be obtained or is unreliable since the patient is a baby or an infant. The visual acuity test includes a binocular visual acuity test and a monocular visual acuity test. The visual field test includes a binocular visual field test and a monocular visual field test. Moreover, in this visual function testing device, a display that presents a visual target image has a dichoptic function. In such a way, the visual function testing device can switch and implement the monocular visual test and the binocular visual test without using an occluder or the like. Note that the visual target to be presented by the visual function testing device is an image or a video presented for the purpose of the visual function tests, and mentioned are a Landolt ring in the visual acuity test, a radiant of the visual field test, and the like.

First, a description is made of a visual function testing device for testing a binocular visual acuity and a binocular visual field as visual function test items by itself.

A description is made of a technical significance of this visual function testing device. In the conventional visual function tests, there have been testers dedicated for each of the visual function test items. Accordingly, in the case of performing the plurality of visual function tests, such problems have occurred that a tester operator and a patient must move among the testers, the tester operator must learn different testing methods, and that test results cannot be integrated. Heretofore, there has been proposed a technology for realizing the visual acuity test and the visual field test in such a manner that a visual target for the visual acuity test is presented on a liquid crystal screen arranged on a center portion, and that a visual target for the visual field test is presented by a light source arranged on a periphery thereof (Japanese Patent Laid-Open Publication No. 2003-93344). However, this technology does not have a function to change a display size and display position of the visual target image in response to a viewpoint distance. Therefore, a viewpoint position is fixed, and the viewpoint position cannot be changed for each of the visual function test items. In a general visual acuity test, a viewpoint distance between a visual acuity chart and an observer is defined to be 5 meters (m).

Moreover, in the visual field test, a capability of presenting the visual target within an approximate range where a viewing angle is 20 degrees to 30 degrees is required in order to measure a central visual field. The viewing angle is one in which a visible range is represented by an angle from an eye, and is a value that represents how wide a range visible from the front is.

That is to say, as shown in FIG. 1, when the visual acuity and field tests are implemented by the same device at a fixed viewpoint position P, a presentation surface 2a in which a viewing angle from a viewpoint position P apart therefrom by a distance A of 5 m is 20 degrees or more becomes necessary. Then, a range of this presentation surface 2a becomes a circle in which a diameter B is approximately 1.76 m. When this circle in which the diameter B is approximately 1.76 m is presented by a display (aspect ratio is 4:3), a screen size of 116 inches (4:3=breadth 2.358 m: height 1.769 m) or more is required. As described above, a configuration in which the viewpoint position P is fixed is not realistic since a scale of a device configuration becomes large.

In this connection, upon receiving the viewpoint distance and visual angle of the observer, the present visual function testing device can calculate a display size and display position of the visual target image, which correspond to the change of the viewpoint position P, and can implement the binocular visual acuity test and the binocular visual field test at an arbitrary viewpoint position P.

Figure 2:
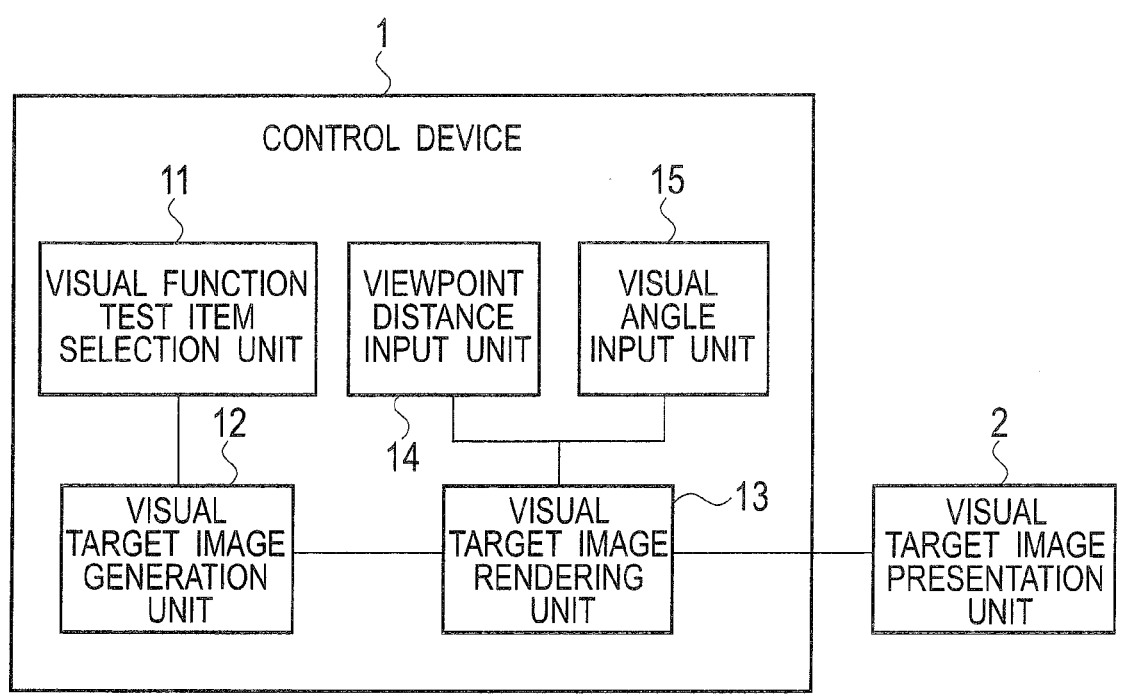
FIG. 2 is a block diagram showing a configuration example of a visual function testing device to be shown as a first embodiment.

The visual function testing device as described above is configured, for example, as shown in FIG. 2. The visual function testing device includes a control device 1 and a visual target image presentation unit 2 such as a liquid crystal display, which presents the visual target image.

Figure 3:
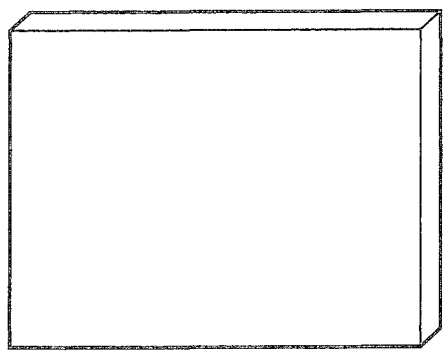
FIGS. 3(a) to 3(d) are views showing examples of a shape of the presentation surface of the visual target image presentation unit.
Figure 3:
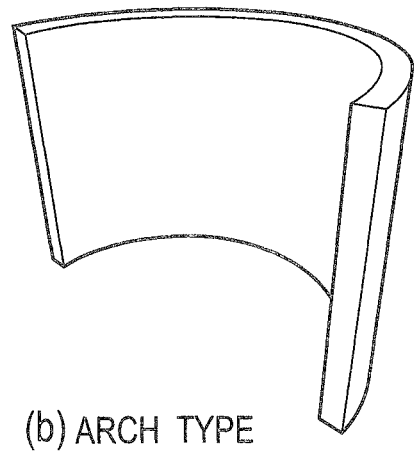
Figure 3:
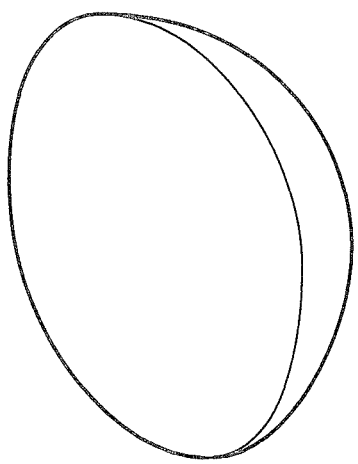
Figure 3:
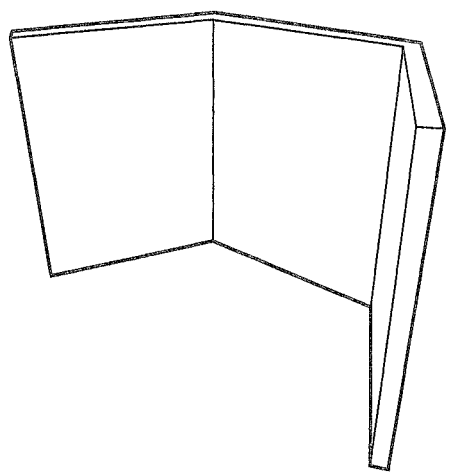

The visual target image presentation unit 2 displays the visual target image. As shown in FIGS. 3(a) to 3(d), a shape of the presentation surface of the visual target image presentation unit 2 may include a flat type as shown in FIG. 3(a), an arch type as shown in FIG. 3(b), and a dome type as shown in FIG. 3(c). Moreover, the shape concerned may include a multi-surface type as shown in FIG. 3(d), in which flat-type displays are combined with one another, or may be composed of a head-mount type such as a head mount display. Note that the multi-surface type is composed of a polygon, and the number of surfaces is not limited to three.

Such a flat-type display has a feature that it is possible to present a high-resolution image. Such arch-type and dome-type displays can effectively cover the visual field, and accordingly, have a feature that it is possible to present a wide-visual-field image. Such a multi-surface type display has a feature that it is possible to present a high-resolution and wide-visual-field image. Moreover, such a head-mount type display has a feature that it is possible to present an image without being affected by external light. Note that, since this visual function testing device takes the viewpoint distance as an input value, desirably, the head of the observer is fixed by mounting a chin rest and the like so that the viewpoint position (head position of the observer) cannot fluctuate.

The control device 1 includes: a visual function test item selection unit 11; a visual target image generation unit 12; a visual target image rendering unit 13; a viewpoint distance input unit 14; and a visual angle input unit 15. These respective units are realized in such a manner that a CPU executes a program and the like, which are stored in a ROM.

The visual function test item selection unit 11 selects the item of the visual function test. As the visual function test item of FIG. 1, either of the binocular visual acuity and the binocular visual field is selected. The visual function test item selection unit 11 may include, for example, a keyboard and the like, which operate the control device 1. In the visual function test item selection unit 11, an operation of selecting any from the visual function test items displayed on the visual target image presentation unit 2 is performed for the keyboard. In such a way, the visual function test item selection unit 11 supplies information of the selected visual function test item to the visual target image generation unit 12.

The visual target image generation unit 12 generates a visual target image corresponding to the test item selected by the visual function test item selection unit 11. The visual target image generation unit 12 outputs the visual target image, which is selected by the visual function test item selection unit 11 from among a plurality of prestored visual target images, to the visual target image rendering unit 13. Moreover, every time when the visual function test item is selected, the visual target image generation unit 12 may newly generate the visual target image. Note that, in the case of using the Landolt ring or a complicated pattern (animal picture, text or the like) as the visual target image, desirably, the Landolt ring or the complicated pattern is generated in advance. Furthermore, a simple pattern such as the radiant may be generated in real time.

In the case where the visual acuity test is selected, the visual target image generation unit 12 generates a Landolt ring as shown in FIG. 4(a). The Landolt ring is a circle of which part is broken, and is a standard visual target for the visual acuity test. When a break with a width of 1.5 mm in the Landolt ring with a diameter of 7.5 millimeters (mm) can be seen from a place apart therefrom by 5 m, visual acuity at that time becomes 1.0. In the case where the visual field test is selected, the visual target image generation unit 12 generates a radiant as shown in FIG. 4(b). With regard to this visual target image, a display size C thereof is adjusted as will be described later.

The viewpoint distance input unit 14 inputs the distance between the visual target image presentation unit 2 and the viewpoint of the observer. The viewpoint distance input unit 14 may include, for example, the keyboard and the like, which operate the control device 1. In the viewpoint distance input unit 14, by visual recognition, input of the viewpoint distance between the viewpoint position of the observer and the visual target image presentation unit 2 is performed for the keyboard. In such a way, the viewpoint distance input unit 14 supplies the inputted viewpoint distance to the visual target image rendering unit 13.

The visual angle input unit 15 inputs the angle made by the visual target image and the viewpoint of the observer. That is to say, the visual angle input unit 15 inputs such a visual angle which the observer requires in order to see the visual target image. The visual angle input unit 15 may include, for example, the keyboard and the like, which operate the control device 1. In the visual angle input unit 15, input of the visual angle is performed for the keyboard. In such a way, the visual angle input unit 15 supplies the inputted visual angle to the visual target image rendering unit 13.

The visual target image rendering unit 13 renders the visual target image to be presented to the visual target image presentation unit 2. At this time, based on the viewpoint distance inputted by the viewpoint distance input unit 14 and on the visual angle inputted by the visual angle input unit 15, the visual target image rendering unit 13 calculates the display size and display position of the visual target image, which correspond to the visual acuity or field test selected by the visual function test item selection unit 11. Then, the visual target image rendering unit 13 renders the visual target image with the calculated display size at the calculated display position. In such a way, on the visual target image presentation unit 2, the visual target image with the display size corresponding to the inputted viewpoint distance and visual angle can be displayed at such a display position of the visual target image presentation unit 2 concerned, which corresponds to the inputted viewpoint distance and visual angle.

[Calculation Processing for Display Size]

Next, a description is made of processing for calculating the display size of the visual target image based on the viewpoint distance and the visual angle.

Figure 5:
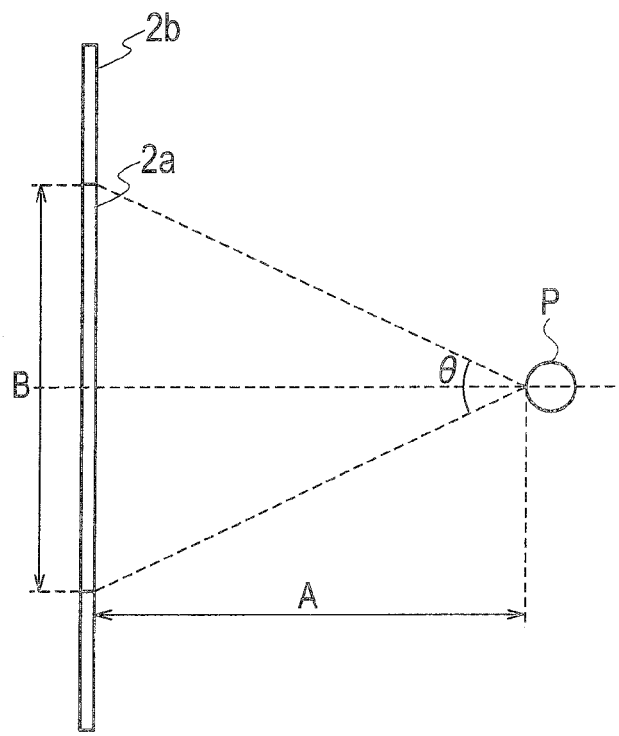
FIG. 5 is a side view explaining a size viewable at a visual angle θ from the viewpoint position P on the visual target image presentation unit.

As shown in FIG. 5, from the viewpoint distance A between the viewpoint position P of the observer and the presentation surface 2a of the visual target image presentation unit 2, and from trigonometric functions (Expression 1a, Expression 1b) of the visual angles θ in the lateral direction and the longitudinal direction, lateral and longitudinal sizes B of the visual target image to be presented on the presentation surface 2a of the visual target image presentation unit 2 are calculated. Expressions 1a and 1b are established as follows:

$$B_W = 2 \times A \times \tan(\theta_W/2) \quad \text{(Expression 1a)}$$

$$B_H = 2 \times A \times \tan(\theta_H/2) \quad \text{(Expression 1b)}$$

where $B_W$ is a lateral size [mm], $B_H$ is a longitudinal size [mm], $\theta_W$ is a lateral visual angle [degree], and $\theta_H$ is a longitudinal visual angle [degree]. Note that, in FIG. 5, a screen of the visual target image presentation unit 2, which is other than the visual angle θ of the observer, is shown as a non-presentation surface 2b.

In the case where the visual target image is square, the display size C just needs to be decided by using a visual angle in at least one direction between the longitudinal direction and the lateral direction in which visual angles are inputted by the visual angle input unit 15. However, in the case where the shape of the visual target image is a shape other than the square, it is necessary to input the visual angles in both of the longitudinal direction and the lateral direction by the visual angle input unit 15 in order to decide the display size C of the visual target image concerned. Alternatively, the visual angle in one of the directions is inputted by the visual angle input unit 15, and further, the aspect ratio (4:3 and the like) is inputted by other means, whereby it is necessary to decide the display size C of the visual target image with the shape other than the square.

Figure 4:
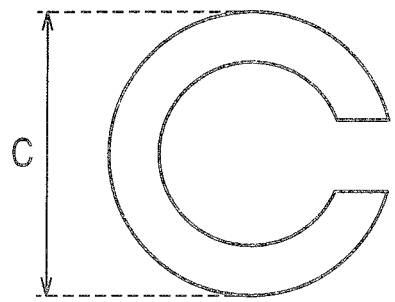
FIGS. 4(a) to 4(c) are views showing visual target images to be presented to the visual target image presentation unit.
Figure 4:
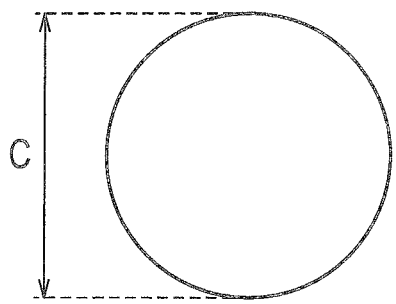
Figure 4:
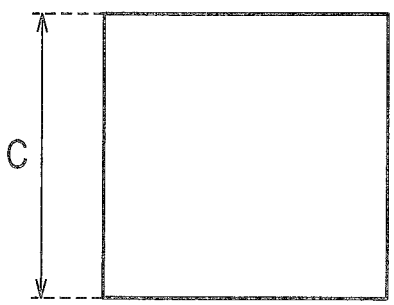

As shown in FIG. 4(*c*), in the case where the size of the visual target image to be generated by the visual target image generation unit 12 is designated as the lateral and longitudinal sizes C [mm], display magnifications D [%] of the visual target image to be presented on the presentation surface 2*a* of the visual target image presentation unit 2 are calculated by Expression 2a and Expression 2b, which are described below. In Expressions 2a and 2b, $C_W$ is the size [pixel] in the lateral direction, $C_H$ is the size [mm] in the longitudinal direction, $D_W$ is such a lateral display magnification [%] of the visual target image, and $D_H$ is such a longitudinal display magnification [%] thereof. The lateral size $B_W$ and the longitudinal size $B_H$ are obtained by Expression 1.

$$D_W = B_W / C_W \quad \text{(Expression 2a)}$$

$$D_H = B_H / C_H \quad \text{(Expression 2b)}$$

If this visual target image rendering unit 13 renders the visual target image by the display magnifications D, then the visual target image rendering unit 13 can present the display size C, which corresponds to the visual angle inputted by the visual angle input unit 15, on the visual target image presentation unit 2. In such a way, even if a resolution of the visual target image presentation unit 2 is different, the visual function testing device can present the visual target image with the display size, which corresponds to the visual angle θ and the viewpoint distance, in conformity with the size of the pixels of the visual target image presentation unit 2 concerned.

There is also a case where the size of the visual target image to be generated by the visual target image generation unit 12 is designated by lateral and longitudinal resolutions E [longitudinal pixels×lateral pixels]. In this case, based on lateral and longitudinal screen dimensions F [mm] of the visual target image presentation unit 2, and on lateral and longitudinal screen resolutions G of the visual target image presentation unit 2, lengths C of the visual target image are calculated by Expressions 3a and 3b. In Expressions 3a and 3b, $E_W$ is the lateral resolution of the visual target image, $E_H$ is the longitudinal resolution thereof, $F_W$ is the lateral screen dimension of the visual target image presentation unit 2, $F_H$ is the longitudinal screen dimension thereof, $G_W$ is the lateral screen resolution of the visual target image presentation unit, and $G_H$ is the longitudinal screen resolution thereof.

$$C_W = E_W \times F_W / G_W \quad \text{(Expression 3a)}$$

$$C_H = E_H \times F_H / G_H \quad \text{(Expression 3b)}$$

The visual target image rendering unit 13 substitutes the display sizes, which are calculated by Expressions 3a and 3b, into Expressions 2a and 2b. In such a way, the visual target image rendering unit 13 can calculate the display magnifications D of the visual target image to be presented on the screen of the visual target image presentation unit 2. If the visual target image rendering unit 13 renders the visual target image by the magnifications thus calculated, then the visual target image rendering unit 13 concerned can present the visual target image at the display sizes C corresponding to the visual angle.

[Calculation Processing for Display Position]

Next, a description is made of processing for calculating the display position of the visual target image based on the viewpoint distance and the visual angle.

Figure 6:
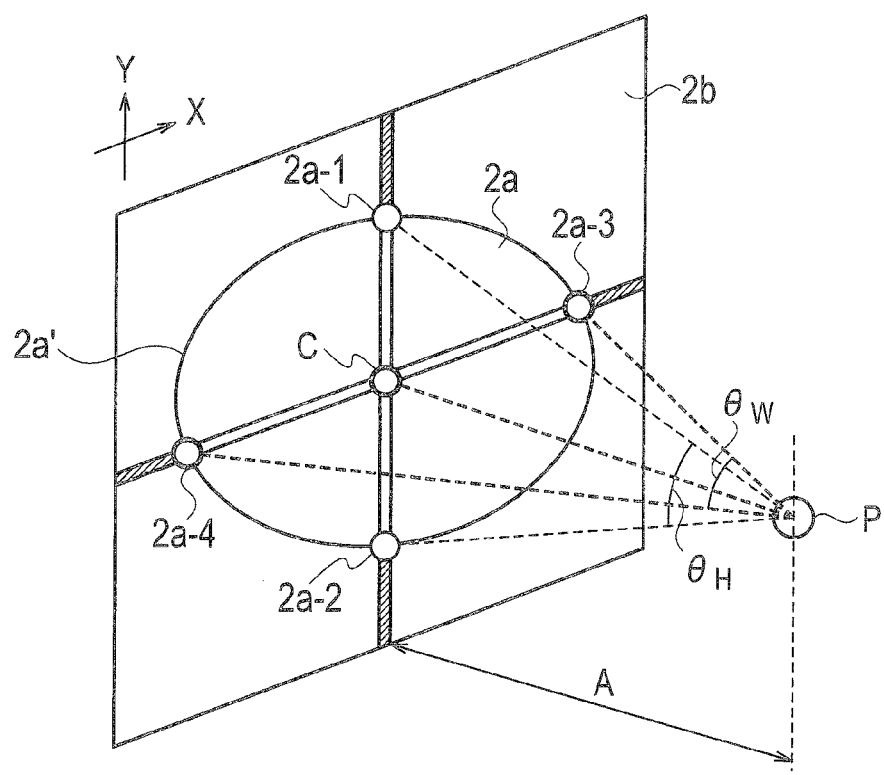
FIG. 6 is a perspective view explaining a display position of the visual target image on the visual target image presentation unit.

As shown in FIG. 6, the display position of the visual target image is designated by an XY coordinate system that takes, as an origin, a screen center of the visual target image presentation unit 2. FIG. 6 shows a state where the viewpoint position P of the observer is directly confronted to the screen center C ($X_0$, $Y_0$) of the presentation screen 2*a* of the visual target image presentation unit 2. The viewpoint distance between the viewpoint position P and the screen center C becomes A. Coordinate values (X, Y) of intersection points 2*a*-1 to 2*a*-4 between a range 2*a*′, which is represented by the visual angles $\theta_W$ (lateral direction) and $\theta_H$ (longitudinal direction) of the observer, and an X-axis and a Y-axis on the presentation surface 2*a* of the visual target image presentation unit 2 are calculated by Expressions 4a and 4b, which are described below.

$$X = \pm A \times \tan(\theta_W/2) - X_0 \quad \text{(Expression 4a)}$$

$$Y = \pm A \times \tan(\theta_H/2) - Y_0 \quad \text{(Expression 4b)}$$

By Expressions 4a and 4b, a coordinate value $X_1$ of the intersection point 2*a*-3, a coordinate value $X_2$ of the intersection point 2*a*-4, a coordinate value $Y_1$ of the intersection point 2*a*-1 and a coordinate value $Y_2$ of the intersection point 2*a*-2 can be calculated while taking, as a center, the screen center C (origin) on the presentation surface 2*a* of the visual target image presentation unit 2. The intersection points are four in total, in which two are located on positive and negative sides on the X-axis, respectively, and other two are located on positive and negative sides on the Y-axis, respectively.

Figure 7:
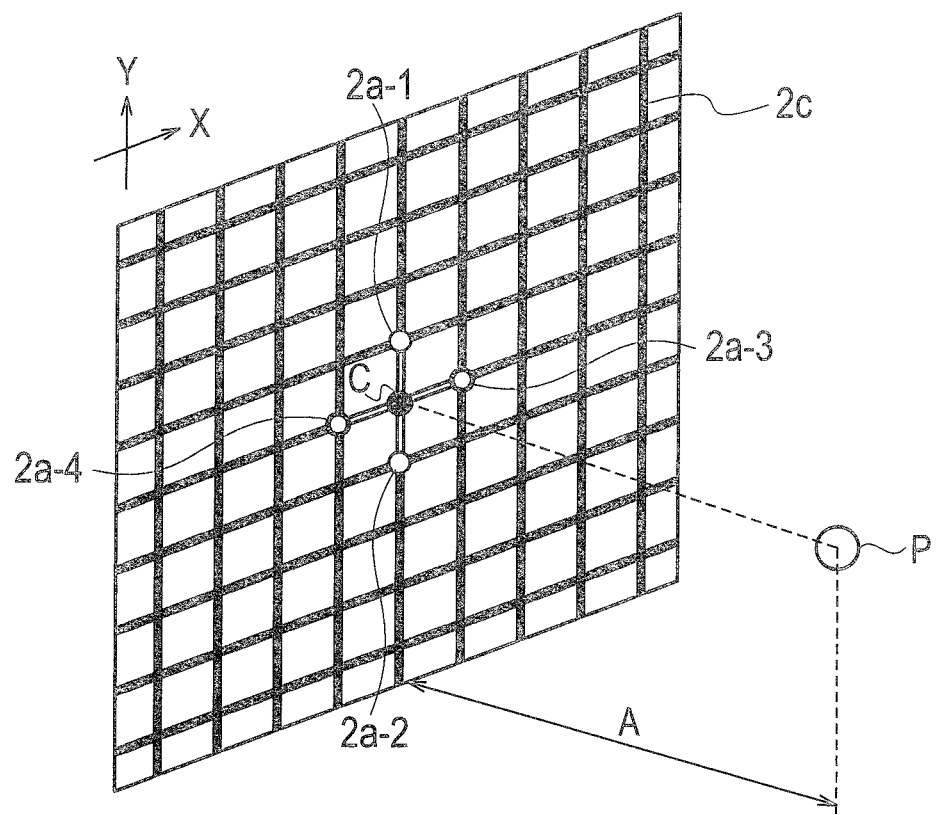
FIG. 7 is a perspective view explaining that the visual target image is arranged on grid lines on the visual target image presentation unit.

As shown in FIG. 7, cross-ruled grid lines 2*c* are set, which take, as references, squares formed of the origin as the screen center C on the presentation surface 2*a* of the visual target image presentation unit 2, and of the four coordinate values [($X_1$, 0), ($X_2$, 0), (0, $Y_1$), (0, $Y_2$)]. Coordinates on the X-axis and the Y-axis, which are apart from the origin by one square, become boundaries of a viewing angle of the visual angle θ in which the origin is taken as a fixation point. Coordinates on the X-axis and the Y-axis, which are apart from the origin by two squares, become boundaries of a viewing angle 2θ in which the origin is taken as the fixation point. That is to say, the respective lattice points on the grid lines 2*c* are set on a display position of the visual target image, whereby, based on the viewpoint distance and the visual angle, which are inputted by the viewpoint distance input unit 14 and the visual angle input unit 15, unit grid widths with respect to the X-axis and the Y-axis can be calculated, and such a cross-ruled coordinate system can be formed. Thereafter, the visual target image rendering unit 13 just needs to designate on which lattice point the visual target image is to be displayed.

In this visual function testing device, input values of the visual angles in the lateral direction (X-axis direction) and the longitudinal direction (Y-axis direction) to the visual angle input unit 15 may be individually set. In the case where both of the visual angles in the lateral direction (X-axis direction) and the longitudinal direction (Y-axis direction), which are inputted by the visual angle input unit 15, are the same, a shape of the lattices to be formed of the grid lines 2*c* becomes square. In the case where the visual angles in the lateral direction (X-axis direction) and the longitudinal direction (Y-axis direction), which are inputted by the visual angle input unit 15, are different from each other, the shape of the lattices to be formed of the grid lines 2*c* becomes rectangular.

Figure 8:
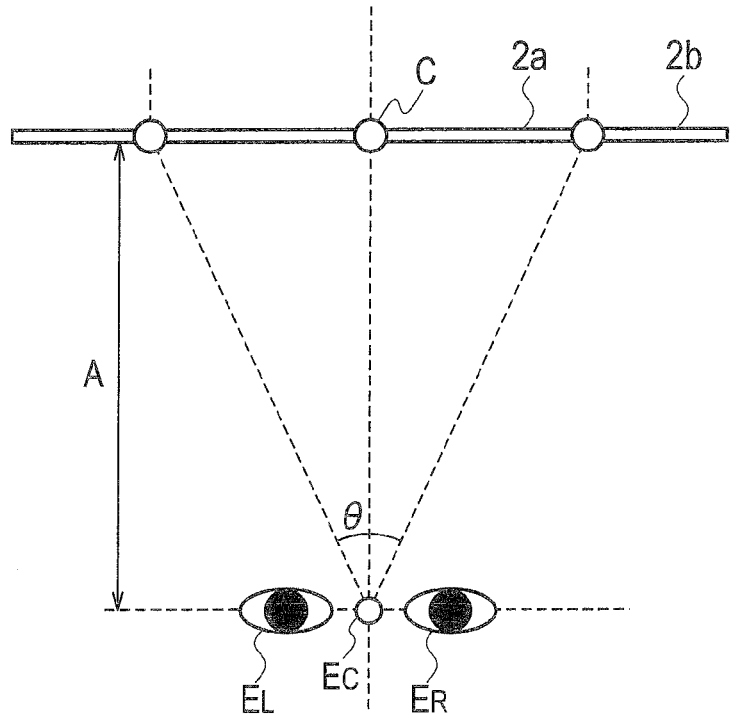
FIGS. 8(a) and 8(b) are top views explaining a screen center to be set with respect to the viewpoint position.
Figure 8:
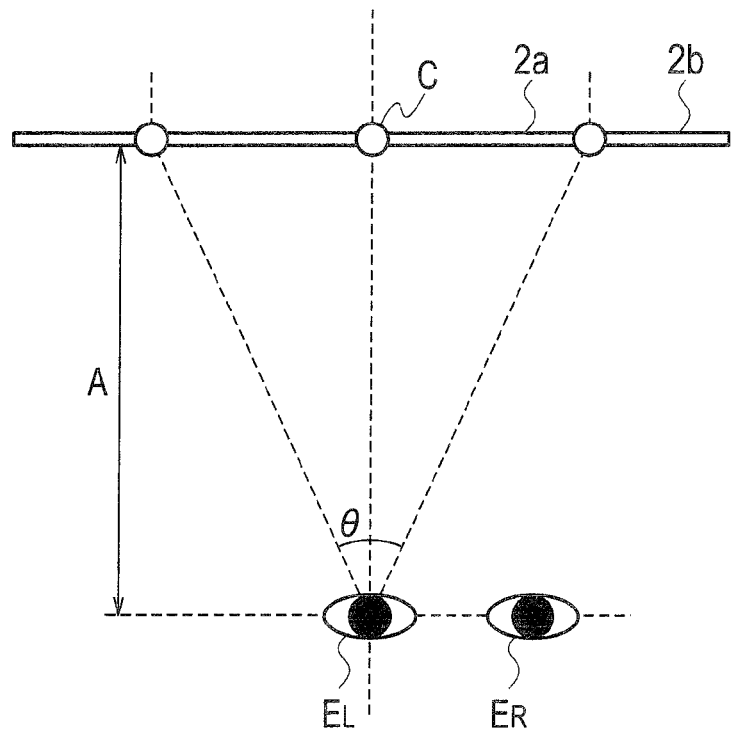

The origin of the presentation surface 2*a* is not limited to the screen center C on the presentation surface 2*a* of the visual target image presentation unit 2. For example, as shown in FIG. 8(*a*), a position C on the presentation surface 2*a*, which is directly confronted to a center position $E_C$ between a position $E_L$ of a left eye between both eyes and a position $E_R$ of a right eye between both of them may be set as the origin. Moreover, as shown in FIG. 8(*b*), the origin may be set on a position C on the presentation surface 2*a*, which is directly confronted to such a left eye position $E_L$ or such a right eye position $E_R$. Furthermore, the origin may be set on an arbitrary position on the presentation surface 2*a*. As a calculation method of the unit grid widths when the origin is set as described above, distance differences between the newly set origin and the screen center C on the presentation surface 2*a* of the visual target image presentation unit 2 are adapted to the four coordinate values ($X_1$, $X_2$, $Y_1$, $Y_2$) calculated by Expressions 4a and 4b. That is to say, such a distance difference in the X-axis direction is added to Expression 4a, and such a distance difference in the Y-axis direction is added to Expression 4b.

[Visual Acuity Test]

Next, a description is made of the visual acuity test by the above-mentioned visual function testing device.

Figure 9:
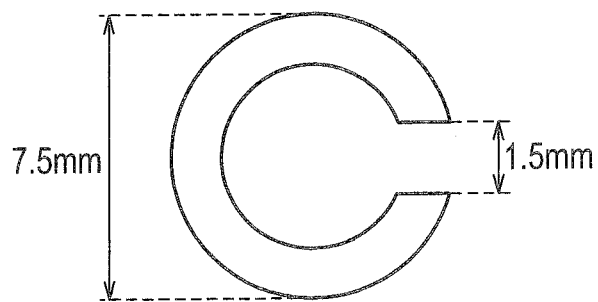
FIG. 9 is a view showing a specific example of the Landolt ring.

The visual acuity test is a test method of evaluating a capability (minimum resolvable threshold) of resolving and recognizing two points or two lines. An angle made by two points or two lines, which are barely determinable by an eye, with respect to the eye is represented by a "minute (=1/60 degrees)", and an inverse number thereof is evaluated as visual acuity. As the existing test method, when a break with a width of 1.5 mm in the Landolt ring with a diameter of 7.5 millimeters (mm) and a thickness of 1.5 mm can be seen from a place apart therefrom by 5 m, visual acuity at that time becomes 1.0. In this case, as shown in FIG. 9, the break with a width of 1.5 mm is equivalent to one minute of the visual angle.

In the visual acuity test, based on the viewpoint distance inputted by the viewpoint distance input unit 14 and on the visual angle inputted by the visual angle input unit 15, the control device 1 sets the display size and display position of the visual target image (for example, the Landolt ring). With regard to the display size, a size corresponding to the visual acuity is set. With regard to the display position, an arbitrary position may be set; however, a center position of the visual target image presentation unit 2 is desirable. Note that, with regard to the above-mentioned visual function test, the binocular visual acuity test is implemented as the visual acuity test since such a blocking function to present the visual target image for each eye is not provided. The monocular visual acuity test is realizable by a visual function testing device to be described later.

In the visual acuity test of the visual function testing device of this embodiment, a resolution width between two points or two lines is set by the visual angle θ corresponding to the visual acuity J as shown in Expression 5 to be described below. The visual angle θ is inputted by the visual angle input unit 15. Then, the visual function testing device presents the visual target image with the display size C fitted to the visual angle θ concerned on the visual target image presentation unit 2.

$J = 1/\theta$ (Expression 5)

Moreover, the visual function testing device adds a function to calculate the visual angle θ from the visual acuity J by back calculation of Expression 5. In such a way, the display size C can be calculated from the visual acuity J.

Shown below is a method for displaying the Landolt ring with a diameter of 7.5 mm, a thickness of 1.5 mm and a break of 1.5 mm so that the break of 1.5 mm can be visually recognized as a visual angle of 1 minute from the viewpoint distance of A m (so as to establish a display size that enables the visual acuity of 1.0 to be tested). Here, the visual target image generation unit 12 generates the Landolt ring in response to that the visual function test item selection unit 11 selects the visual acuity test.

(1) In the event of generating the visual target image by the visual target image creation unit 12, the size of the visual target image (Landolt ring) is designated by the length C. At this time, a calculation method of the display magnifications D for measuring desired visual acuity by seeing the visual target image presentation unit 2 from the viewpoint distance inputted by the viewpoint distance input unit 14 is as follows.

In a general visual acuity test, while the width (resolution width) of the break of the Landolt ring is 1.5 mm, the diameter of the Landolt ring is defined as 7.5 mm (5 times). Therefore, in order to display the break of the Landolt at the visual angle of 1 minute (1/60 degrees) on the visual target image presentation unit 2, the visual target image of the Landolt ring just needs to be displayed at a visual angle of 5 minutes (5 times). The size B of the visual target image to be visually recognized at the visual angle of 5 minutes from the viewpoint distance of A m is calculated from Expression 1 by using the visual angle θ=5 minutes. Note that, in the case where the visual target image is the Landolt ring, the lateral and longitudinal length B of the Landolt ring are equal to each other, and accordingly, only either one of the lateral and longitudinal lengths B just needs to be obtained. Then, such a display magnification D of the Landolt ring on the visual target image presentation unit 2 is calculated from either one of Expressions 2a and 2b by using this length B of the visual target image and the designated size C of the visual target image.

(2) In the event of generating the visual target image by the visual target image generation unit 12, the size of the visual target image (Landolt ring) is designated by an image resolution E. At this time, the calculation method of the display magnifications D for measuring desired visual acuity by seeing the visual target image presentation unit 2 from the viewpoint distance inputted by the viewpoint distance input unit 14 is as follows.

In a similar way to (1), the size B of the visual target image to be visually recognized with a size of the visual angle θ of 5 minutes from the viewpoint distance of A m is calculated by Expression 1. Note that, in the case where the visual target image is the Landolt ring, the lateral and longitudinal length B of the Landolt ring are equal to each other, and accordingly, only either one of the lateral and longitudinal lengths B just needs to be obtained. From either one of Expressions 3a and 3b, the size B of the visual target image, which is designated by the image resolution E, is converted into the display size C from such a screen dimension F and screen resolution G of the visual target image presentation unit 2, and further, from either one of Expressions 2a and 2b, the display magnification D is calculated from the size B of the visual target image and the display size C.

If the resolution width (break) of the visual target (Landolt ring) displayed on the visual target image presentation unit 2 can be perceived under the display magnification D calculated by (1) or (2), then the visual acuity is 1.0. In order to establish a test condition similar to that of the current visual acuity test, the viewpoint distance A between the visual target image presentation unit 2 and the observer just needs to be set at 5 m.

[Visual Field Test]

The visual field test is a test for measuring a sensitivity distribution map of the vision by a response of a subject to the presentation of the visual target. In this visual field test, the visual function testing device measures a perceivable range without moving the eye. A visual field measurement method includes dynamic visual field measurement and static visual field measurement. In the dynamic visual field measurement, the visual target is moved, and a region where certain sensitivity is exhibited is measured. In the static visual field measurement, the sensitivity is measured at fixed points without moving the visual target.

In the visual field test, based on the viewpoint distance inputted by the viewpoint distance input unit 14 and on the visual angle value inputted by the visual angle input unit 15, the control device 1 sets the display size and display position of the visual target image (for example, the radiant). The display size just needs to be set at an arbitrary visual angle. The display position is set on a lattice in which a fixation point is taken as an origin, and a grid width is set by the viewpoint distance and the visual angle. Note that, with regard to the above-mentioned visual function test, the binocular visual field test is implemented as the visual field test since such a blocking function to present the visual target image for each eye is not provided. The monocular visual field test is realizable by a visual function testing device to be described later.

Figure 10:
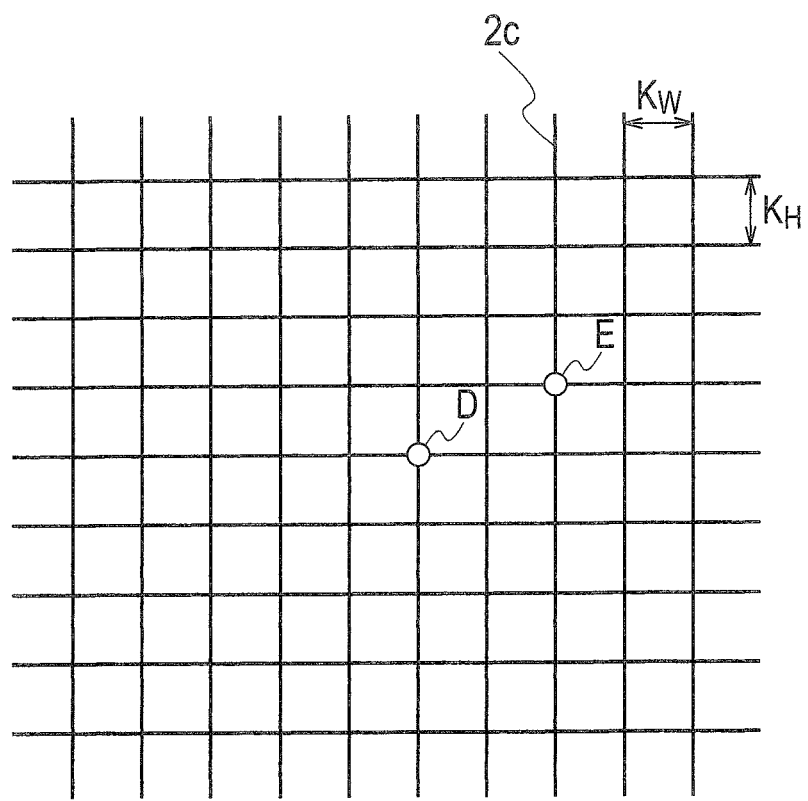
FIG. 10 is a front view showing a state where the visual target image as the radiant is arranged with respect to an origin on the grid lines of the visual target image presentation unit.

In the visual field test of the visual function testing device of this embodiment, as shown in FIG. 10, the observer allows a fixation point D as the origin to be displayed on the visual target image presentation unit 2. The observer gazes this fixation point D. In a state where the viewpoint of the observer is fixed as described above, the visual target E (radiant) is displayed on a position on the lattice in which the fixation point D is taken as the origin. In such a way, the visual function testing device tests whether or not the observer can perceive the visual target E.

The fixation point D as the origin and the visual target E are displayed on intersection points on grid lines 2c with a grid width K, which are formed on the visual target image presentation unit 2. The grid lines 2c are similar to those shown in FIG. 7 mentioned above. This grid width K is calculated based on the visual distance A and the visual angle θ in accordance with the above-described Expression 4 ($X=\pm A\times \tan(\theta/2)-X_0, Y=\pm A\times\tan(\theta/2)-Y_0$).

Moreover, with regard to a visual target position to be set on the intersection point of the grid lines 2c, the visual function testing device can arbitrarily set a display order of the visual target. That is to say, the visual function testing device can display the visual target image in a random display order within a range of a visual field desired to be measured. Moreover, the visual function testing device may limit the display position of each visual target image to an arbitrary range.

Furthermore, in a similar way to a quantitative dynamic visual field test, this visual function testing device may create a plurality of visual targets (radiants) with arbitrary display size and brightness value in advance, and may implement the visual field test by changing the size and brightness of the visual targets. In such a way, the visual function testing device can test perception sensitivity in the visual field test.

Note that, in a similar way to the visual field test, designation of the display position of the visual target image in the visual acuity test is performed by designating the lattice point on which the visual target image is to be displayed. In the usual visual acuity test, the visual acuity target (Landolt ring) is displayed on the screen center C of the visual target image presentation unit 2; however, in the course of the visual acuity test, the visual acuity target is sometimes displayed on a position apart from the screen center C. For example, in such a case of testing visual acuity when the observer faces upward, the Landolt ring is displayed on a lattice point shifted upward from the screen center C.

As described above, in accordance with the visual function testing device shown as the first embodiment, based on the viewpoint distance and the visual angle, the display size and display position of the visual target image are calculated, and the visual target image is rendered. Accordingly, the plurality of visual function tests can be performed by the same device in a state where both eyes are opened and a state where the visual performance is close to the daily one without blocking the visual field or restricting the viewing field.

Second Embodiment

Next, a description is made of a visual function testing device according to a second embodiment. Note that the same reference numerals are assigned to similar portions to those of the above-mentioned first embodiment, whereby a detailed description thereof is omitted.

The visual function testing device to be shown as the second embodiment is a device that can perform visual function tests of monocular visual acuity, monocular visual field and stereopsis in addition to those performed by the visual function testing device shown as the above-mentioned first embodiment.

Figure 11:
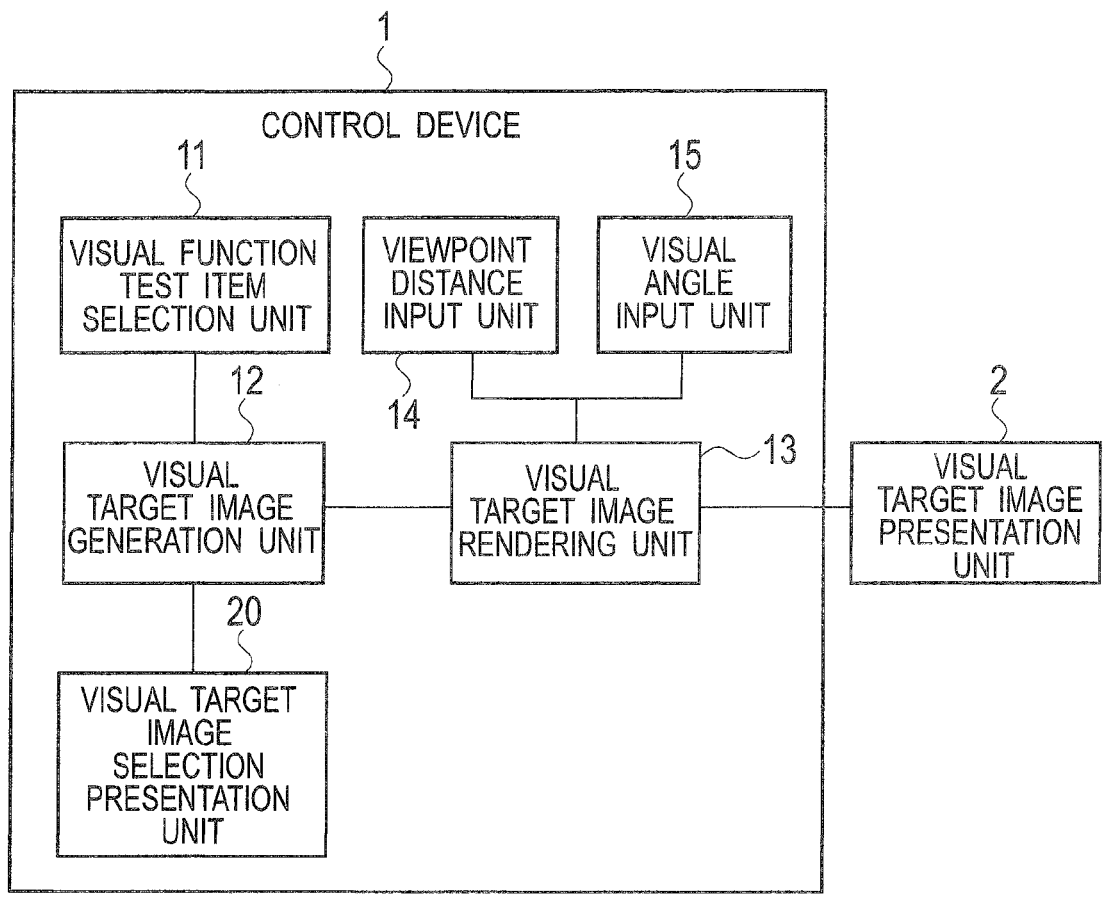
FIG. 11 is a block diagram showing a configuration example of a visual function testing device to be shown as a second embodiment.

As shown in FIG. 11, this visual function testing device is different from the above-mentioned visual function testing device in that a visual target image selection presentation unit 20 is provided in the control device 1. Moreover, in this visual function testing device, the visual target image generation unit 12 has a binocular visual target image generation function to generate visual target images for each of the right eye and left eye of the subject. Furthermore, the visual target image presentation unit 2 has a dichoptic visual target image presentation function to perform dichoptic viewing for the binocular visual target images for the right eye and the left eye, which are generated by the binocular visual target image generation function of the visual target image generation unit 12, and to present the binocular target images, which are subjected to the dichoptic viewing, for each of the eyes corresponding thereto.

This visual target image presentation unit 2 can allow the right eye and left eye of the observer to separate and visually recognize a right eye-use visual target image and a left eye-use visual target image, respectively. The visual target image presentation unit 2 may include, for example, a display and a projection system, which use the current dichoptic method such as a polarization method, a spectrum method, and a time division method, and may be composed of a head-mount type such as a head mount display. The observer is allowed to put on glasses corresponding to the method to be adopted by the visual target image presentation unit 2. In such a way, the visual function testing device includes a dichoptic function to present visual target images, which are different from each other, individually to the right eye and left eye of the observer.

The visual target image selection presentation unit 20 selects display or non-display of the right-eye or left-eye visual target image, which is to be presented by the dichoptic visual target image presentation function of the visual target image presentation unit 2, independently of each other. The visual target image selection presentation unit 20 may include, for example, a keyboard and the like. In the visual target image selection presentation unit 20, an operation of selecting either of the display and non-display of the right-eye or left-eye visual target image displayed on the visual target image presentation unit 2 is performed for the keyboard. In such a way, the visual target image selection presentation unit 20 supplies information on the selected display or non-display to the visual target image generation unit 12.

In the visual function testing device as described above, the visual target image selection presentation unit 20 displays a visual target image corresponding to the monocular visual acuity test, the monocular visual field test or the stereopsis test, which is selected by the visual function test item selection unit 11.

Specifically, in the visual function testing device, the monocular visual acuity test, the monocular visual field test or the stereopsis test is selected by the visual function test item selection unit 11. Then, the visual target image generation unit 12 generates the right eye-use visual target image and the left eye-use visual target image, which correspond to the test thus selected (binocular visual target image generation function).

In the case where the visual function test only for one eye is selected by the visual target image section presentation unit 20, the visual target image generation unit 12 generates the selected right eye-use visual target image or left eye-use visual target image, and supplies the generated right eye- or left eye-use visual target image to the visual target image rendering unit 13. In the case where the stereopsis test is selected, the visual target image generation unit 12 generates both of the right eye-use visual target image and the left eye-use visual target image, and supplies the generated right eye- and left eye-use visual target images to the visual target image rendering unit 13.

The visual target image generation unit 12 generates both of the right eye-use visual target image and the left eye-use visual target image, and converts one of the visual target images, which is selected as the non-display by the visual target image selection presentation unit 20, into a blank image with the same color as a background color.

Note that the visual target image selection presentation unit 20 may be connected to the visual target image rendering unit 13, and may allow the visual target image rendering unit 13 to render only the right eye-use visual target image or the left eye-use visual target image. Moreover, the visual target image selection presentation unit 20 may be connected to the visual target image presentation unit 2, and may allow the visual target image presentation unit 2 to display only the right eye-use visual target image or the left eye-use visual target image.

The visual target image rendering unit 13 individually renders the right eye-use visual target image and the left eye-use visual target image, which are supplied from the visual target image generation unit 12 (dichoptic image rendering function). Rendering data corresponding to the right eye-use visual target image and rendering data corresponding to the left eye-use visual target image are supplied to the visual target image presentation unit 2.

By using the rendering data individually corresponding to the right eye-use visual target image and the left eye-use visual target image, the visual target image presentation unit 2 displays the right eye-use visual target image and the left eye-use visual target image (dichoptic image presentation function). In such a way, the right eye-use visual target image is visually recognized only by the right eye of the observer, and the left eye-use visual target image is visually recognized by the left eye of the observer.

In the visual function testing device as described above, in the monocular visual acuity test and the monocular visual field test, generation of the visual target image and setting of the display size and the display position are performed in a similar way to the above-mentioned visual function testing device. Then, the right eye-use visual target image or the left eye-use visual target image is made visually recognizable in accordance with the selection of the visual target image selection presentation unit 20, whereby the monocular visual acuity test and the monocular visual field test are realized.

Next, a description is made of the stereopsis test by the visual function testing device shown in FIG. 11. In the stereopsis test, a relative depth perception to be caused by fusing images with a binocular parallax, which are individually presented to the left and right eyes, is tested. This parallax is a positional change of image formation on a retina owing to a movement of a relative position between the eye and an object or to a difference therebetween. With regard to this parallax, whether the object is near or far can be perceived by the binocular parallax represented by an angle made by lines of sight of both eyes with respect to the object.

In the stereopsis test, with regard to the display size C of the visual target image, the arbitrary size B just needs to be set based on the visual angle inputted by the visual angle input unit 15. Moreover, in the stereopsis test, with regard to the display position, a center-to-center distance (parallax) between the visual target images of the left and the right eye is set based on the visual angle inputted by the visual angle input unit 15.

Figure 12:
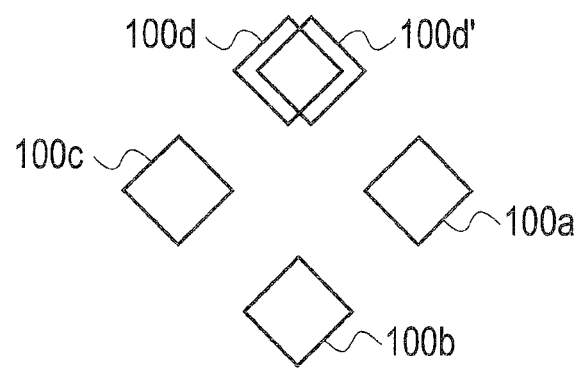
FIG. 12 is a view showing an example of displaying a visual target image provided with a parallax.

In this stereopsis test of the visual function testing device, as shown in FIG. 12, among a plurality of dichoptic visual target images 100a to 100d presented on the visual target image presentation unit 2, an arbitrary parallax amount is imparted to one visual target image denoted by reference numerals 100d and 100d'.

Figure 13:
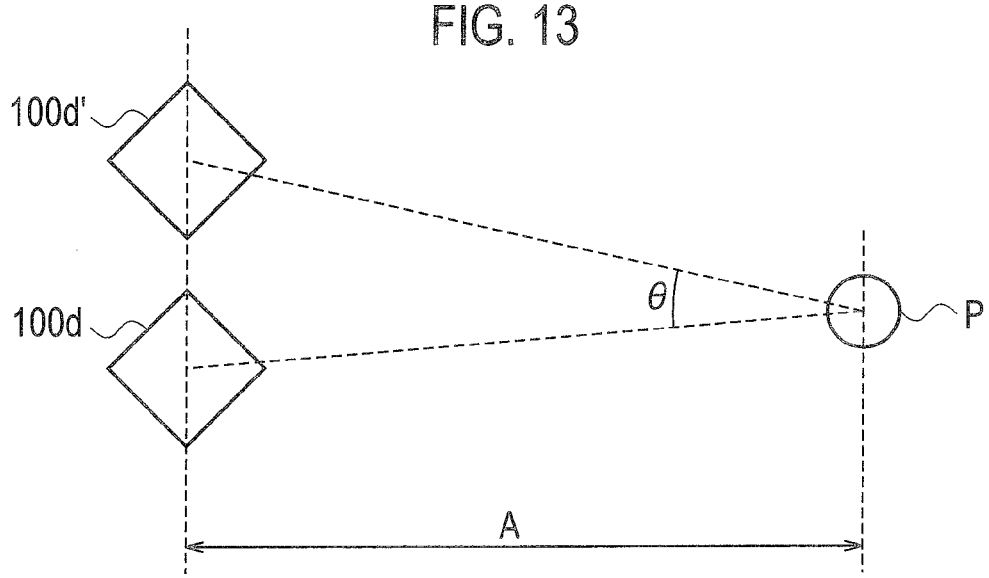
FIG. 13 is a view explaining a distance corresponding to the parallax at a time of displaying the visual target image provided with the parallax.

The display size C of such a visual target image 100 is calculated by Expression 2 or Expression 3, which is described above, in such a manner that an arbitrary size is set by the visual angle $\theta$ inputted by the visual angle input unit 15. Moreover, with regard to the parallax amount that allows the recognition of the stereopsis, as shown in FIG. 13, the visual angle $\theta$ inputted by the visual angle input unit 15 is set, and the display position is calculated by the viewpoint distance A inputted by the viewpoint distance input unit 14. As described above, the visual function testing device inputs the visual angle $\theta$ and the viewpoint distance A, and can thereby adjust such a distance between the visual target images 100d and 100d' for testing the stereopsis. In such a way, such a stereoscopic function can be tested based on whether or not there is a relative depth perception with respect to a micro parallax amount.

In accordance with this visual function testing device, by the dichoptic image presentation function of the visual target image presentation unit 2, the functions of the monocular visual acuity and the monocular visual field can be tested in a state where both eyes are opened without restricting the visual field, and in addition, the stereopsis test can be implemented by the same device.

Third Embodiment

Next, a description is made of a visual function testing device according to a third embodiment. Note that the same reference numerals are assigned to similar portions to those of the above-mentioned embodiments, whereby a detailed description thereof is omitted.

This visual function testing device is a device that can perform visual function tests of a binocular vision and an eye position in addition to those performed by the visual function testing device shown as the above-mentioned second embodiment.

Such a binocular vision test is a test that evaluates whether or not images given to the retinas of the respective left and right eyes can be seen as a single image in a central nervous system of vision (brain), and the test is performed for each of items such as simultaneous vision, (sensory, motor) fusions, stereopsis, and retinal correspondence.

The simultaneous vision refers to a capability of recognizing two types of images A and B as one image at the time of seeing the image A by the right eye and seeing the image B by the left eye. Moreover, the stereopsis is a capability of stereoscopically seeing an object by recognizing the parallax to be caused by that positions of the left and right eyes are different from each other. The fusion is further classified into the motor fusion and the sensory fusion. The motor fusion is a capability of recognizing a left eye-use image and a right eye-use image, which are presented at positions apart from each other, as one image by eye movements as congestion (cross eye) and divergence (separate eye). The sensory fusion is a capability of recognizing the same image, which is changed in appearance such as a size and a blur difference and is presented to the left and right eyes, as one image by a function of the brain.

Figure 14:
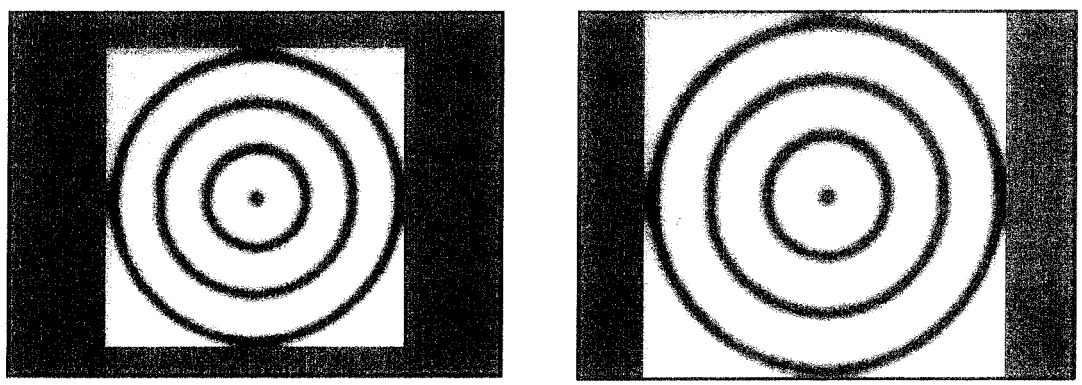
FIG. 14 is a view explaining human sensory fusion, and is an explanatory view about a capability of recognizing, as an image, those in which a same image is changed in size and presented to left and right eyes.
Figure 15:
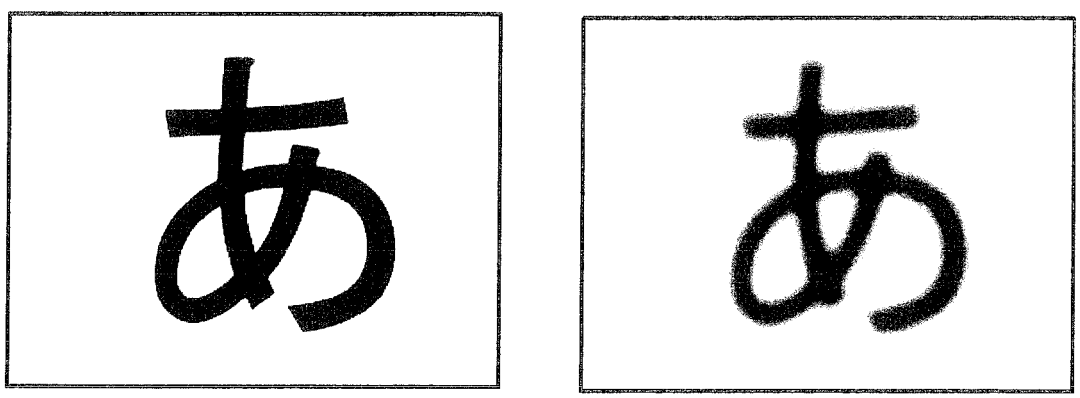
FIG. 15 is a view explaining the human sensory fusion, and is an explanatory view about a capability of recognizing, as an image, those in which a same image is changed in blur difference and presented to the left and right eyes.

For example, in the sensory fusion test, with regard to a test (aniseikonia test) of a size difference between visual target sizes shown in FIG. 14, to a test of the blur difference between visual targets shown in FIG. 15, and to a test for a positional shift, a right eye-use visual target image and a left eye-use visual target image, between which the blur difference is inherent, are generated in advance. Then, in a similar way to the visual function testing device shown as the above-mentioned second embodiment, the right eye-use visual target image and the left eye-use visual target image, which are generated by the visual function test item selection unit 11, are rendered by the visual target image rendering unit 13, and by the visual target image presentation unit 2, the right eye-use visual target image and the left eye-use visual target image are displayed in accordance with a predetermined dichoptic method. In such a way, the visual function testing device allows only the right eye of the observer to visually recognize the right eye-use visual target image, and allows only the left eye of the observer to visually recognize the left eye-use visual target image.

Figure 16:
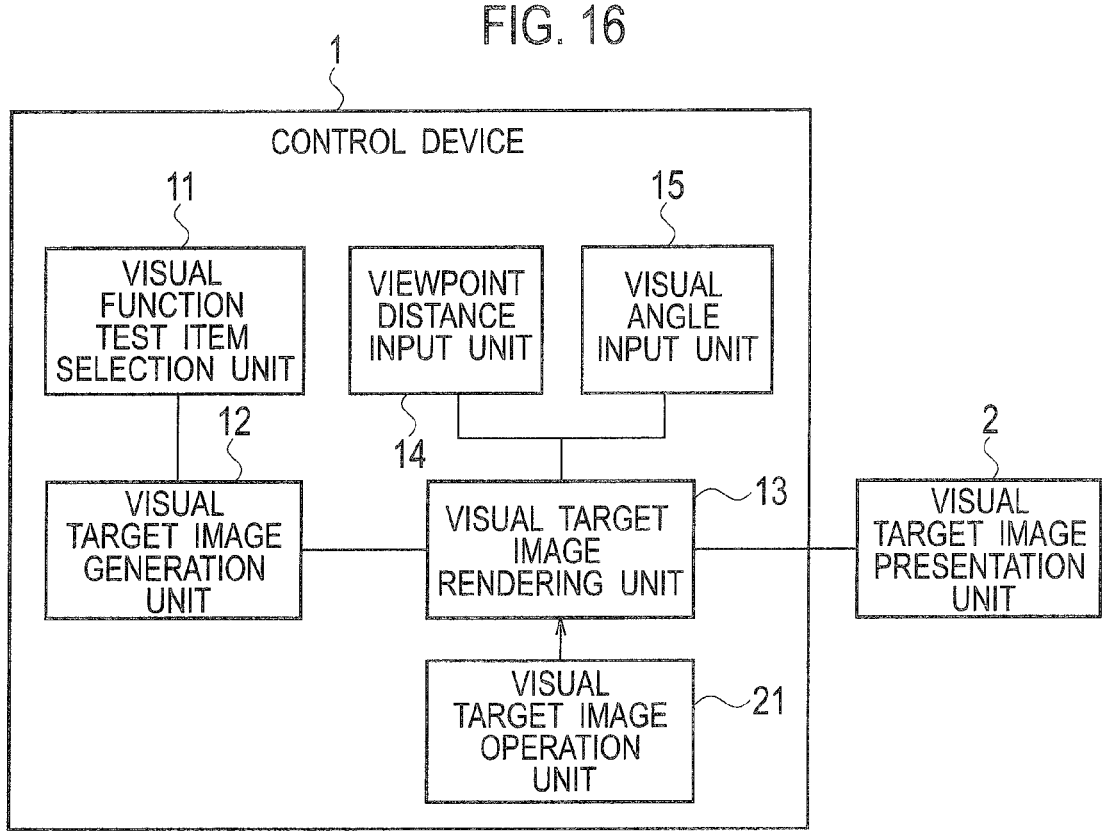
FIG. 16 is a block diagram showing a configuration example of a visual function testing device to be shown as a third embodiment.

As shown in FIG. 16, this visual function testing device includes a visual target image operation unit 21. This visual target image operation unit 21 changes at least either of the display size and display position of the visual target image by an operation of a user. The visual target image operation unit 21 is composed of an operation device such as a mouse and a button, which is operated by the user, and outputs a signal of allowing the user to move the visual target image, which is presented by the visual target image presentation unit 2, in response to visual performance of the visual target image concerned. Then, the visual target image rendering unit 13 updates the position of the visual target image, which is to be presented on the visual target image presentation unit 2, based on the signal supplied from the visual target image operation unit 21.

In the visual function testing device as described above, the binocular vision test or the eye position test is selected by the visual function test item selection unit 11. In this case, in accordance with the display size or display position of the visual target image, which is changed by the visual target image operation unit 21, the visual target image rendering unit 13 changes the visual target image to the display size and the display position, which is calculated by the visual target image rendering unit 13, and then renders the visual target image concerned.

As described above, in accordance with the visual function testing device shown as the third embodiment, the display size and display position of the visual target image can be changed by the operation of the user. In such a way, the visual function testing device becomes capable of performing the binocular vision tests (simultaneous vision test, motor fusion test, sensory fusion test) and the eye position test by itself.

Note that, with regard to grid lines to be displayed at the eye position test, the grid lines 2c are displayed on the presentation surface 2a in a similar way to the visual function testing device shown as the first embodiment.

Next, a description is made of a visual function testing device according to a fourth embodiment. Note that the same reference numerals are assigned to similar portions to those of the above-mentioned embodiments, whereby a detailed description thereof is omitted.

Figure 17:
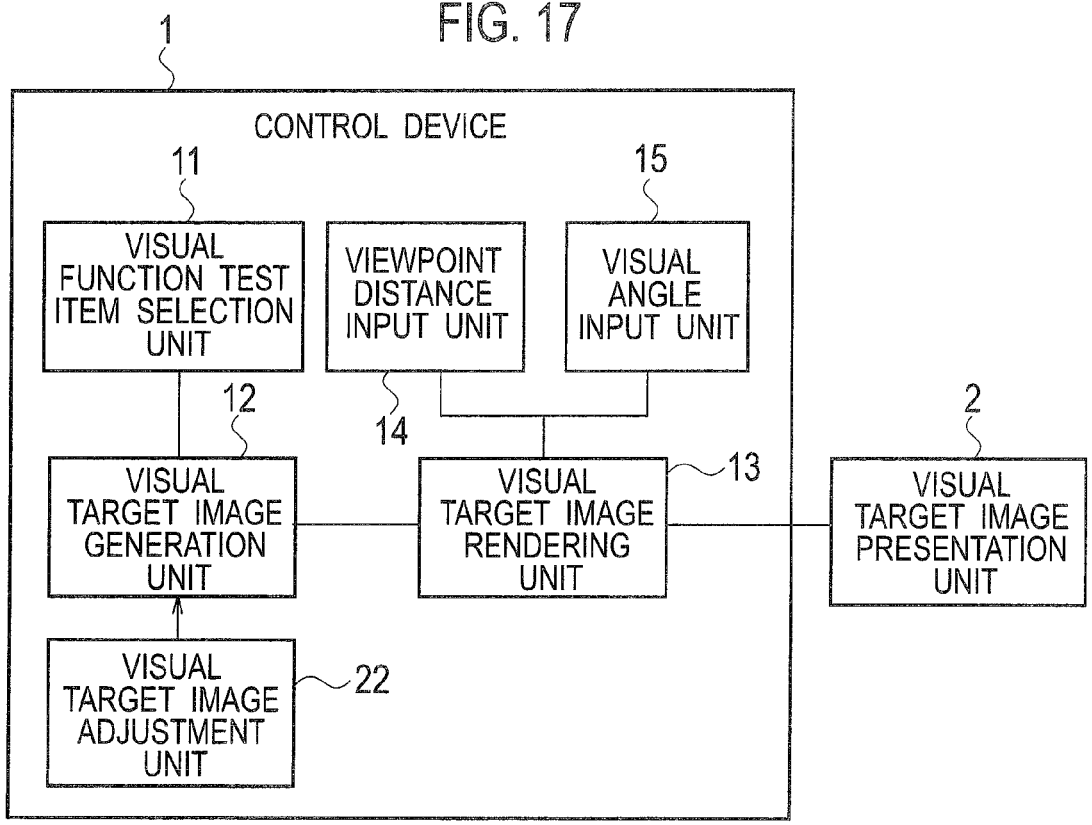
FIG. 17 is a block diagram showing a configuration example of a visual function testing device to be shown as a fourth embodiment.

As shown in FIG. 17, this visual function testing device includes a visual target image adjustment unit 22 that adjusts the visual performance of the visual target image, which is to be presented on the visual target image presentation unit 2, in addition to those performed by the visual function testing devices shown as the above-mentioned embodiments.

The visual target image adjustment unit 22 is a unit for adjusting brightness, contrast, color or transparency of the visual target image. The visual target image adjustment unit 22 supplies a control signal of adjusting the brightness, contrast, color or transparency of the visual target image to the visual target image generation unit 12. For example, the visual target image adjustment unit 22 is composed of an operation device such as a keyboard and a mouse. The visual target image adjustment unit 22 is operated by the user while the user is seeing the visual target image displayed on the visual target image presentation unit 2, and thereby adjusts the visual target image.

Based on the control signal supplied from the visual target image adjustment unit 22, the visual target image generation unit 12 adjusts the brightness, contrast, color or transparency of the visual target image generated in response to the selection of the visual function test item selection unit 11. The adjusted visual target image is supplied to the visual target image rendering unit 13, is then rendered, and is presented to the visual target image presentation unit 2.

In accordance with the visual function testing device as described above, the brightness, contrast, color and transparency of the visual target image are adjusted by the operation of the user, whereby the sensitivity of the visual function can be tested by the change of the visual target image.

Fifth Embodiment

Next, a description is made of a visual function testing device according to a fifth embodiment. Note that the same reference numerals are assigned to similar portions to those of the above-mentioned embodiments, whereby a detailed description thereof is omitted.

Figure 18:
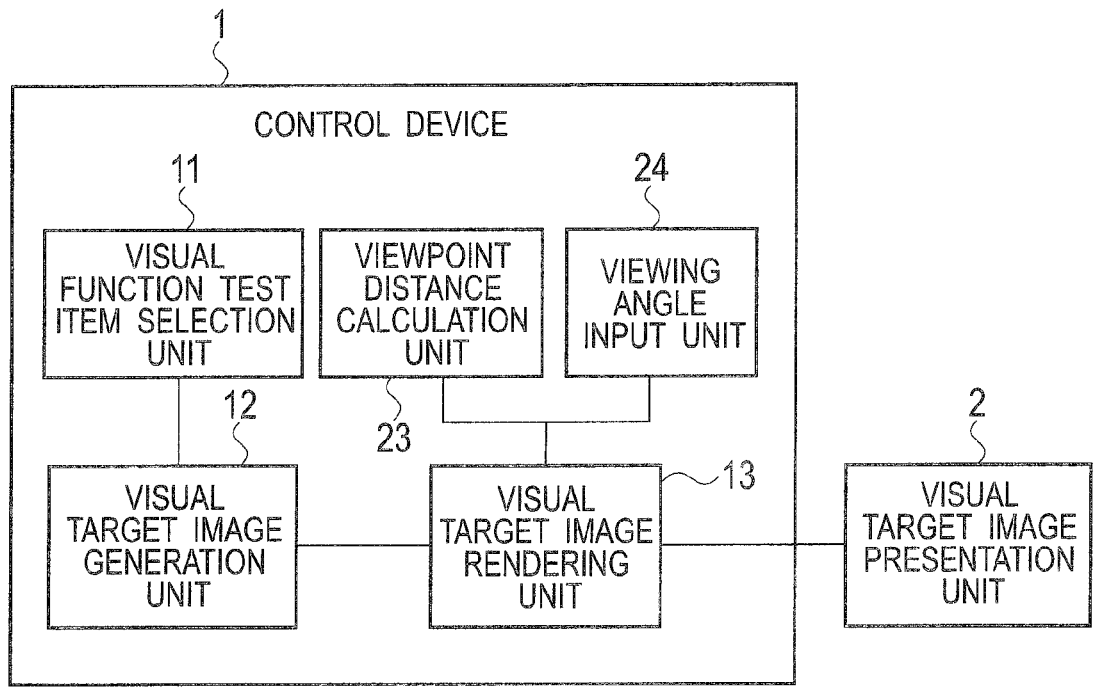
FIG. 18 is a block diagram showing a configuration example of a visual function testing device to be shown as a fifth embodiment.

As shown in FIG. 18, this visual function testing device includes a viewpoint distance calculation unit 23 in place of the viewpoint distance input unit 14, and further, includes a viewing angle input unit 24.

In this visual function testing device, in the case where the visual field test is selected by the visual function test item selection unit 11, the viewing angle input unit 24 inputs a viewing angle desired to be tested in the visual field test concerned. This viewing angle input unit 24 may include, for example, a keyboard, a mouse, a remote controller and the like, which are to be operated by the user, and inputs viewing angle desired to be tested by the user.

The viewpoint distance calculation unit 23 calculates a viewpoint distance necessary to implement the visual field test at the viewing angle, which is inputted by the viewing angle input unit 24, in the screen dimensions of the visual target image presentation unit 2. At this time, as shown in Expression 1 ($B=2 \times A \times \tan(\theta/2)$), the viewpoint distance calculation unit 23 receives θ as the viewing angle inputted by the viewing angle input unit 24. In response to this, the viewpoint distance calculation unit 23 calculates Expression 1 by using 0 as the viewing angle concerned, and calculates the viewpoint distance A.

As described above, in response to that the visual field test is selected, and that the viewing angle desired to be tested is inputted, the visual function testing device can present the viewpoint distance, at which the viewing angle concerned can be tested, to the user. In such a way, in the case where a wide viewing angle is desired to be tested, the visual function testing device can prompt the user to bring the viewpoint position P close to the visual target image presentation unit 2. Hence, in accordance with this visual function testing device, the visual field test can be performed by simple operations without setting complicated conditions.

Sixth Embodiment

Next, a description is made of a visual function testing device according to a sixth embodiment. Note that the same reference numerals are assigned to similar portions to those of the above-mentioned embodiments, whereby a detailed description thereof is omitted.

Figure 19:
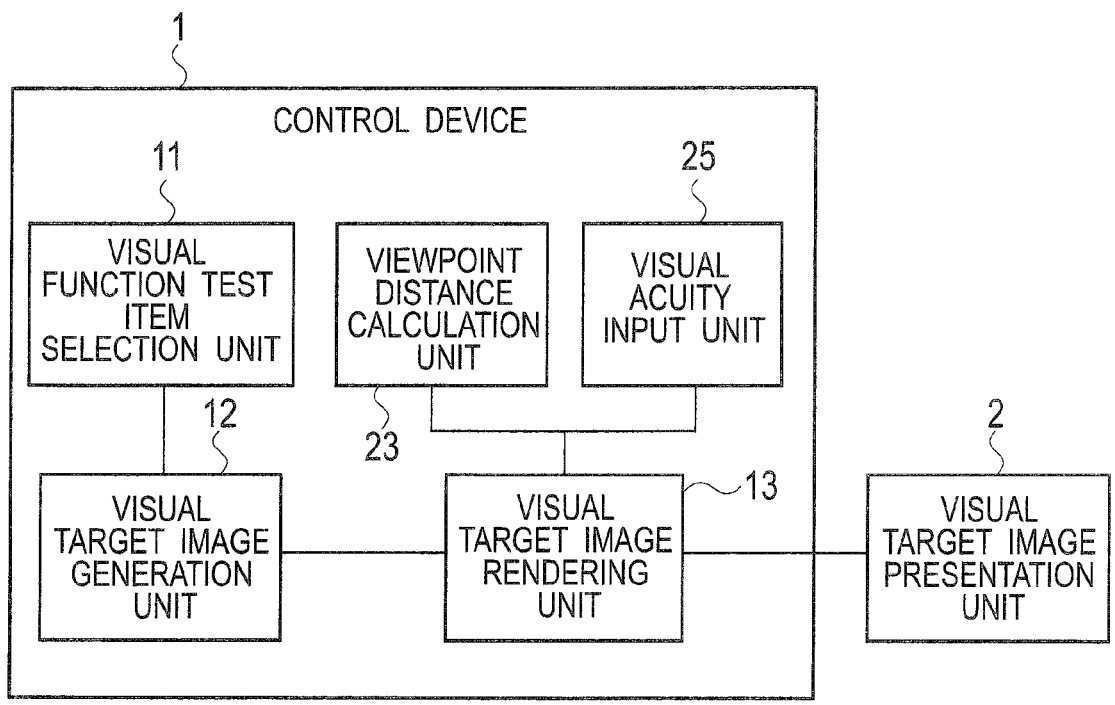
FIG. 19 is a block diagram showing a configuration example of a visual function testing device to be shown as a sixth embodiment.

As shown in FIG. 19, this visual function testing device includes a viewpoint distance calculation unit 23 in place of the viewpoint distance input unit 14, and further, includes a visual acuity input unit 25.

In the case where the visual acuity test is selected by the visual function test item selection unit 11, the visual acuity input unit 25 inputs visual acuity for use in the visual acuity test concerned. This visual acuity input unit 25 may include, for example, a keyboard, a mouse, a remote controller and the like, which are to be operated by the user, and inputs visual acuity desired to be tested by the user.

The viewpoint distance calculation unit 23 calculates the viewpoint distance A required to implement the visual acuity test at the visual acuity, which is inputted by the visual acuity input unit 25, in the resolution of the visual target image presentation unit 2. It is necessary for the viewpoint distance calculation unit 23 to set a shorter viewpoint distance A as the visual acuity desired to be tested is lower, and to calculate a longer viewpoint distance A as the visual acuity desired to be tested is higher.

It is necessary for such an image presentation resolution of the image, which is to be presented by this visual function testing device, to satisfy a predetermined visual acuity conversion value H. This visual acuity conversion value H is a value that indicates to which extent of visual acuity one pixel of the visual target image presentation unit 2 corresponds. This visual acuity conversion value H becomes higher as the image presentation resolution of the visual target image presentation unit 2 is higher since a finer visual target mage can be presented.

In order that the observer can measure the desired visual acuity, a resolution of the visual target image presentation unit 2, which is for allowing distinguishment thereof by the visual acuity concerned, becomes necessary. Hence, in the case where higher visual acuity is desired to be measured for the observer, a higher resolution of the visual target image presentation unit 2 becomes necessary. A description is made below of a calculation method of this visual acuity conversion value H.

The visual acuity is spatial resolving power of the viewing angle. Here, as shown in FIG. 5, an angle (hereinafter, a visual angle) made with respect to the viewpoint position P is defined as θ. As units of this visual angle, a "minute" and a "second" obtained by dividing this "minute" into equal 60 parts are used. A value of this "minute" becomes "60 minutes" in the case where the visual angle θ is 1 degree.

In usual, a minimum value (minimum resolvable threshold) of a distance between two identifiable objects is represented by the visual angle, and an inverse number thereof becomes a visual acuity value. That is to say, visual acuity at which an interval of 1 minute as the visual angle can be identified is defined as 1.0, if an interval of a 0.5 minute can be identified, then the visual acuity value is 2.0, and if only an interval of 2 minutes can be identified, then the visual acuity value is 0.5.

When such a relationship between the visual acuity and the visual angle is applied to presentation resolving power of the image to be displayed by the visual function testing device, then, the minimum resolvable threshold is represented by the size of one pixel. Then, an inverse number of the visual angle (unit: minute) with respect to the size of one pixel becomes the visual acuity.

Hence, a visual acuity conversion value H obtained by converting such image display resolving power into the visual acuity is defined by an image presentation visual angle θ[degree] and an image presentation resolution X [pixel] as shown in Expression 6 to be described below.

$$H=1/((\theta \times 60)/X)=X/(\theta \times 60) \quad \text{(Expression 6)}$$

The image presentation visual angle θ in Expression 6 that represents this visual acuity conversion value H is defined as in Expression 7 and Expression 8 by the distance A [mm] between the observer and the presentation surface 2a.

$$\tan(\theta/2)=(B/2)/A=B/2A \quad \text{(Expression 7)}$$

$$\theta=2 \times \tan^{-1}(B/2A) \quad \text{(Expression 8)}$$

Then, when the visual angle θ of Expression 8 is substituted to Expression 6, then the visual acuity conversion value H is represented as in Expression 9 to be described below.

$$H=X/(2 \times \tan^{-1}(B/2A) \times 60)=X/(120 \times \tan^{-1}(B/2A)) \quad \text{(Expression 9)}$$

That is to say, as shown in Expression 10 to be described below, $$X=120 \times H \times \tan^{-1}(B/2H) \quad \text{(Expression 10)}$$

As described above, if the visual acuity conversion value H desired to be displayed, the width B of the presentation surface 2a, and the distance A between the observer and the presentation surface 2a are specified, then the image presentation resolution X is uniquely determined.

In accordance with this visual function testing device, if the observer inputs the visual acuity (visual acuity conversion value) desired to be tested by the visual acuity test, then the viewpoint distance A for ensuring the distance that enables the visual acuity test concerned can be presented. Hence, in accordance with this visual function testing device, the visual acuity test can be performed by simple operations without setting complicated conditions.

Seventh Embodiment

Next, a description is made of a visual function testing device according to a seventh embodiment. Note that the same reference numerals are assigned to similar portions to those of the above-mentioned embodiments, whereby a detailed description thereof is omitted.

Figure 20:
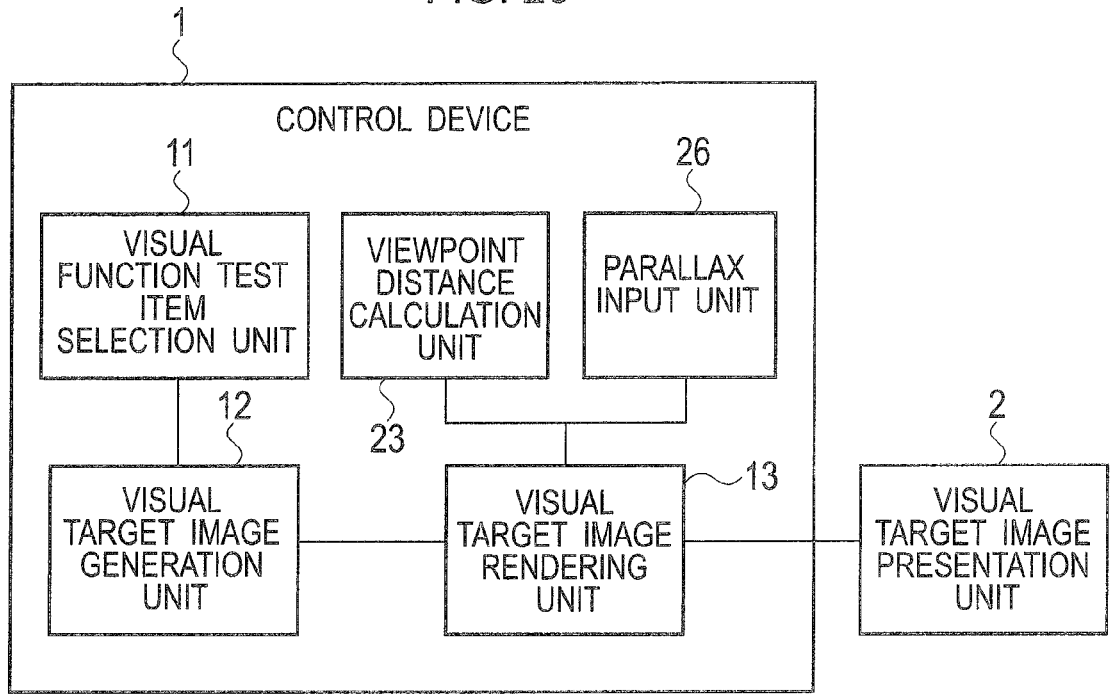
FIG. 20 is a block diagram showing a configuration example of a visual function testing device to be shown as a seventh embodiment.

As shown in FIG. 20, this visual function testing device includes a viewpoint distance calculation unit 23 in place of the viewpoint distance input unit 14, and further, includes a parallax input unit 26.

In the case where the stereopsis test is selected by the visual function test item selection unit 11, the parallax input unit 26 inputs a parallax for use in the stereopsis test concerned. This parallax input unit 26 may include, for example, a keyboard, a mouse, a remote controller and the like, which are to be operated by the user, and inputs a parallax desired to be tested by the user.

The viewpoint distance calculation unit 23 calculates the viewpoint distance A required to implement the stereopsis test at the parallax, which is inputted by the parallax input unit 265, in the resolution of the visual target image presentation unit 2. At this time, the visual function testing device can calculate a minimum presentation visual angle with respect to the viewpoint distance A between the viewpoint position P and the presentation surface 2a by the inverse number of the visual acuity conversion value H in the above-mentioned embodiment. It is necessary for the viewpoint distance calculation unit 23 to set a longer viewpoint distance A as the parallax desired to be tested is smaller, and to calculate a shorter viewpoint distance A as the parallax desired to be tested is larger.

When the parallax desired to be measured by the user is inputted by the parallax input unit 26, the visual function testing device as described above can obtain the viewpoint distance A, which enables the parallax concerned to be measured, by the viewpoint distance calculation unit 23, and can present the viewpoint distance A for ensuring the parallax desired to be tested. Hence, in accordance with this visual function testing device, the stereopsis test can be performed by simple operations without setting complicated conditions.

Eighth Embodiment

Next, a description is made a visual function testing device according to an eighth embodiment. Note that the same reference numerals are assigned to similar portions to those of the above-mentioned embodiments, whereby a detailed description thereof is omitted.

Figure 21:
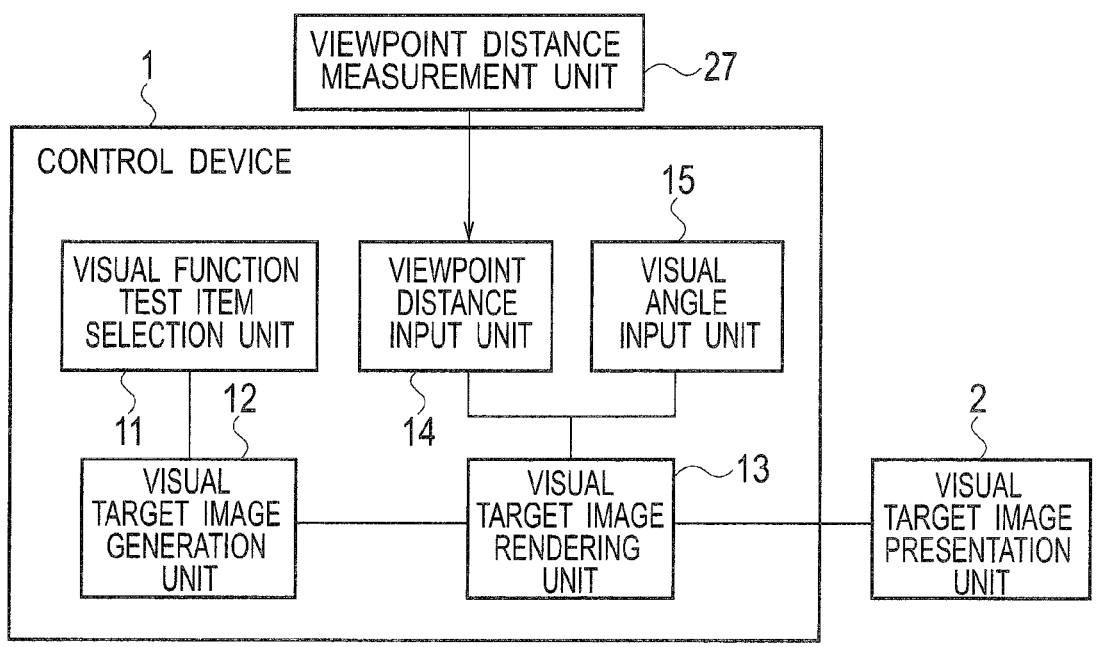
FIG. 21 is a block diagram showing a configuration example of a visual function testing device to be shown as an eighth embodiment.

As shown in FIG. 21, this visual function testing device is a device that further includes a viewpoint distance measurement unit 27 in comparison with the visual function testing device shown as the above-mentioned first embodiment. This viewpoint distance measurement unit 27 measures a distance between the visual target image presentation unit 2 and the viewpoint position P of the observer. The viewpoint distance measurement unit 27 inputs the current viewpoint position P thus measured to the viewpoint distance input unit 14. For example, the viewpoint distance measurement unit 27 measures a head position of the observer, and calculates the viewpoint distance from the head position concerned. Alternatively, the viewpoint distance measurement unit 27 may be a distance sensor provided on dichoptic glasses put on by the observer. In such a way, the viewpoint distance input unit 14 can automatically input the viewpoint distance.

As described above, in accordance with the visual function testing device, it is not necessary to designate the viewpoint position P in advance, and the visual function test corresponding to the head position of the observer or the actual viewpoint position P can be implemented. Moreover, in the above-described embodiments shown in FIG. 18 to FIG. 20, the necessary viewpoint distances A are calculated in response to the viewing angle, the visual acuity and the parallax, which require to be tested, and meanwhile, in accordance with this visual function testing device, a viewing angle, visual acuity and a parallax, for which testing is possible with respect to the current viewing distance A, can be presented on the contrary.

Ninth Embodiment

Next, a description is made of a visual function testing device according to a ninth embodiment. Note that the same reference numerals are assigned to similar portions to those of the above-mentioned embodiments, whereby a detailed description thereof is omitted.

Figure 22:
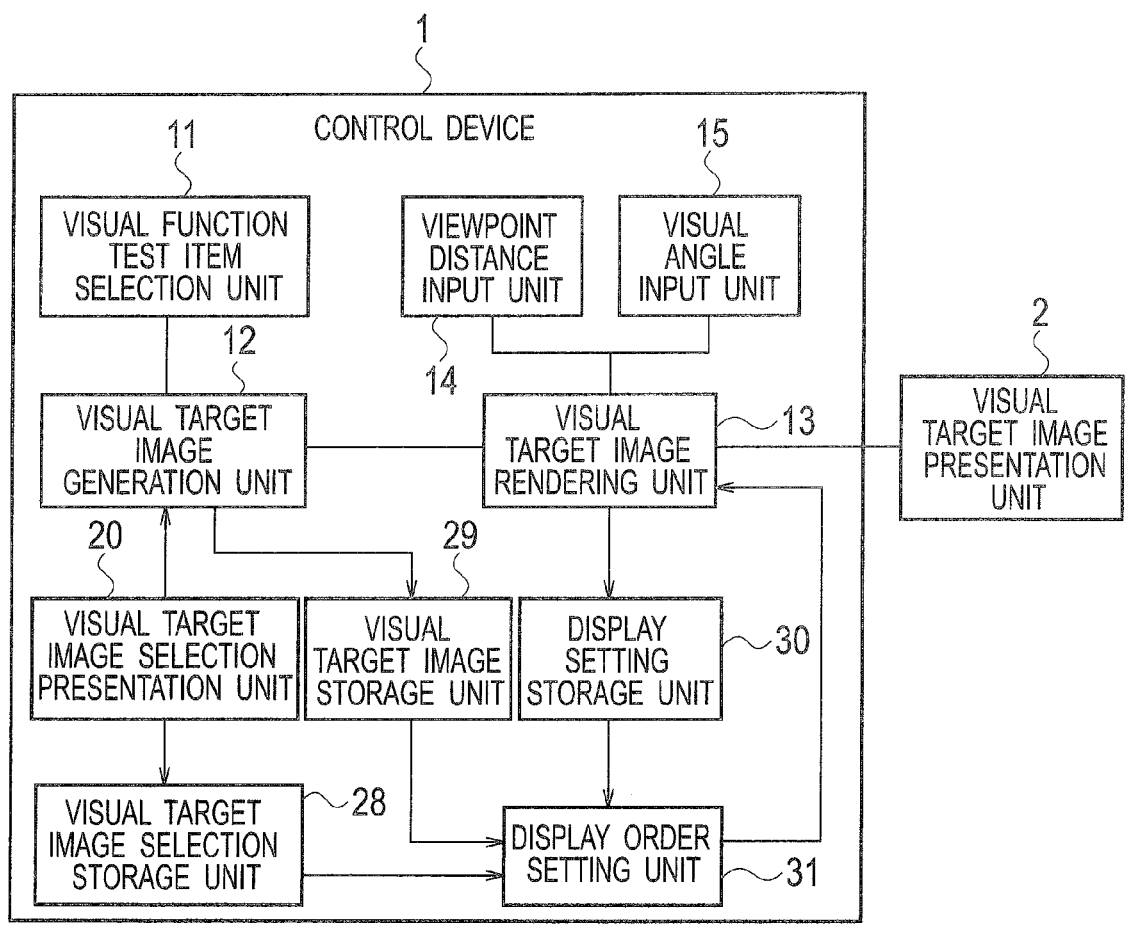
FIG. 22 is a block diagram showing a configuration example of a visual function testing device to be shown as a ninth embodiment.

As shown in FIG. 22, this visual function testing device includes a visual target image selection storage unit 28, a visual target image storage unit 29, a display setting storage unit 30, and a display order setting unit 31 in addition to the constituents of the visual function testing device of the above-mentioned second embodiment.

The visual target image storage unit 29 stores the visual target image generated by the visual target image generation unit 12.

The display setting storage unit 30 stores the display size and display position of the visual target image, which are calculated by using the viewpoint position P inputted by the viewpoint distance input unit 14, and the visual angle inputted by the visual angle input unit 15.

The visual target image selection storage unit 28 stores the display or non-display of the visual target image for each of the right eye and the left eye, which is set by the visual target image selection presentation unit 20.

The display order setting unit 31 receives the information of the display or non-display of the visual target image for each of the right eye and the left eye, which is stored in the visual target image selection storage unit 28, the visual target image stored in the visual target image storage unit 29, and the display size and display position of the visual target image, which is stored in the display setting storage unit 30. Then, by using these data, the display order setting unit 31 sets a display order of the visual target image.

The display order setting unit 31 presents such visual target images corresponding to a plurality of the visual function test items, for example, so that the respective visual function test items can be performed, for example, in an order programmed in advance. Moreover, the visual target images of the respective visual function test items are in a display state, which corresponds to the viewing angle, the visual acuity and the parallax, which are set previously by the observer, and is set by the visual target image selection presentation unit 20.

In the visual function testing device, in accordance with the display order set by the display order setting unit 31, the display order setting unit 31 calls out the visual target images stored in the visual target image storage unit 29, and the visual target images are rendered by the visual target image rendering unit 13. In such a way, the visual function testing device can program a testing order of the plurality of test items, and can mount a function capable of implementing a screening test for a plurality of visual functions in a short time. Hence, for example, when the visual function is desired to be tested after a content video such as a movie is seen by using the visual target image presentation unit 2, then the screening test is only started, whereby the visual target images of the plurality of visual function test items can be presented, and the visual function tests can be implemented.

Tenth Embodiment

Next, a description is made of a visual function testing device according to a tenth embodiment. Note that the same reference numerals are assigned to similar portions to those of the above-mentioned embodiments, whereby a detailed description thereof is omitted.

Figure 23:
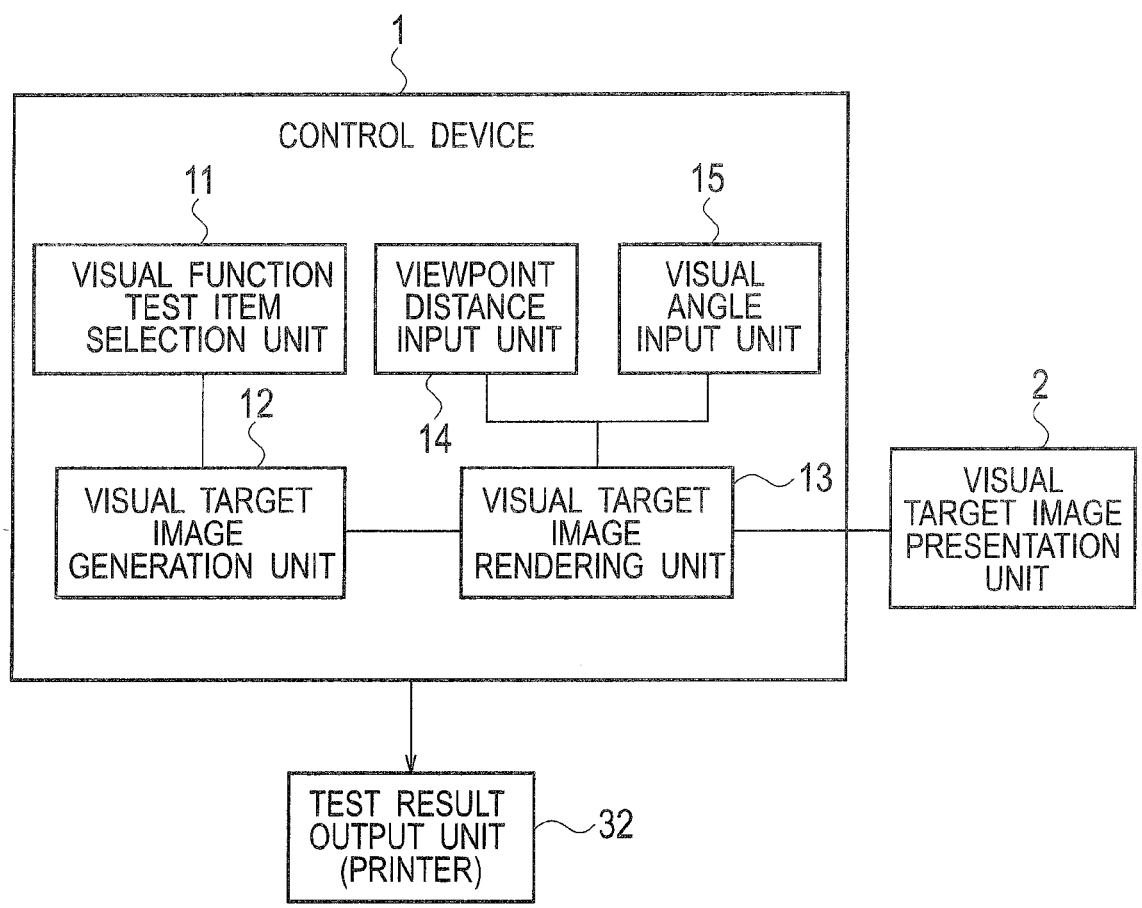
FIG. 23 is a block diagram showing a configuration example of a visual function testing device to be shown as a tenth embodiment.

As shown in FIG. 23, this visual function testing device includes a test result output unit 32, which outputs test results of the visual function tests selected by the visual function test item selection unit 11, in addition to the constituents of the visual function testing devices of the above-mentioned embodiments. This test result output unit 32 outputs the test results, which correspond to the respective visual function test items which can be performed by the visual function test device, in a predetermined format. This predetermined format is a format in which test results of the plurality of visual function test items matched with the preset current test contents can be seen on a printing sheet.

For example, as in the visual function testing device shown as the ninth embodiment, the visual function testing device as described above can present the visual target images of the plurality of visual function test items in a predetermined order, and can output the test results of the visual function test items in response to an operation of the observer. In such a way, even if the observer does not have technical knowledge about the visual function tests, the visual function testing device can draw results of the visual function test results from output results of the test result output unit 32.

Note that the above-mentioned embodiments are merely examples of the present subject matter. Therefore, it is a matter of course that the present subject matter is not limited to the above-mentioned embodiments, and that a variety of modifications are possible in response to the design and the like within the scope without departing from the technical sprit according to the present subject matter even if such modifications are out of the embodiments described above.

INDUSTRIAL APPLICABILITY

In accordance with the present disclosure, it will be industrially applicable to manufacture a visual function testing device that performs the plurality of visual function tests by itself.

REFERENCE SIGNS LIST

1 CONTROL DEVICE
2 VISUAL TARGET IMAGE PRESENTATION UNIT
11 VISUAL FUNCTION TEST ITEM SELECTION UNIT
12 VISUAL TARGET IMAGE GENERATION UNIT
13 VISUAL TARGET IMAGE RENDERING UNIT
14 VIEWPOINT DISTANCE INPUT UNIT
15 VISUAL ANGLE INPUT UNIT
20 VISUAL TARGET IMAGE SELECTION PRESENTATION UNIT
21 VISUAL TARGET IMAGE OPERATION UNIT
22 VISUAL TARGET IMAGE ADJUSTMENT UNIT
23 VIEWPOINT DISTANCE CALCULATION UNIT
24 VIEWING ANGLE INPUT UNIT
25 VISUAL ACUITY INPUT UNIT
26 PARALLAX INPUT UNIT
27 VIEWPOINT DISTANCE MEASUREMENT UNIT
28 VISUAL TARGET IMAGE SELECTION STORAGE UNIT
29 VISUAL TARGET IMAGE STORAGE UNIT
30 DISPLAY SETTING STORAGE UNIT
31 DISPLAY ORDER SETTING UNIT
32 TEST RESULT OUTPUT UNIT

I claim:

1. A device comprising:
a display for displaying a visual target for testing a visual function;
a memory storing a program; and
a processor;
wherein the program, when executed by the processor, causes the processor to determine a size of the visual target and a position where the visual target is displayed on the display, based on a distance between an examinee and the display, and display the visual target with the determined size at the determined position on the display.

2. The device according to claim 1, wherein,
the program causes the processor to determine the size of the visual target and the position where the visual target is displayed on the display, and display the visual target with the determined size at the determined position on the display, corresponding to at least one of a visual acuity test, a visual field test, a stereopsis test, a binocular vision test, and an eye position test.

3. The device according to claim 1, wherein,
the program causes the processor to determine the size of the visual target and the position where the visual target is displayed on the display for each of a right eye and left eye of the examinee, and display the visual target with the determined size at the determined position on the display for each of the right eye and left eye of the examinee, corresponding to the stereopsis test.

* * * * *